(12) United States Patent
Parker et al.

(10) Patent No.: US 10,883,992 B2
(45) Date of Patent: Jan. 5, 2021

(54) UNIVERSAL KINASE SUBSTRATES AND METHODS OF USE THEREOF

(71) Applicants: Regents of the University of Minnesota, Minneapolis, MN (US); Yale University, New Haven, CT (US)

(72) Inventors: Laurie L. Parker, Minneapolis, MN (US); Wei Cui, Minneapolis, MN (US); Benjamin Turk, New Haven, CT (US)

(73) Assignees: Regents of the University of Minnesota, Minneapolis, MN (US); Yale University, New Haven, CT (US)

(*) Notice: Subject to any disclaimer, the term of this patent is extended or adjusted under 35 U.S.C. 154(b) by 0 days.

(21) Appl. No.: 16/283,412

(22) Filed: Feb. 22, 2019

(65) Prior Publication Data
US 2019/0302117 A1 Oct. 3, 2019

Related U.S. Application Data

(60) Provisional application No. 62/633,997, filed on Feb. 22, 2018.

(51) Int. Cl.
*G01N 33/573* (2006.01)
*C07K 7/06* (2006.01)
*G16B 35/20* (2019.01)
*C07K 7/08* (2006.01)

(52) U.S. Cl.
CPC .......... *G01N 33/573* (2013.01); *C07K 7/06* (2013.01); *C07K 7/08* (2013.01); *G16B 35/20* (2019.02); *G01N 2333/912* (2013.01)

(58) Field of Classification Search
CPC ........ C07K 1/13; C07K 2319/21; C07K 7/06; C07K 7/08; C12N 9/00; C12Q 1/485; G01N 2333/912; G01N 2500/00; G01N 33/573; G16B 35/20
See application file for complete search history.

(56) References Cited

U.S. PATENT DOCUMENTS

| | | | |
|---|---|---|---|
| 4,612,302 A | 9/1986 | Szabo et al. | |
| 4,684,620 A | 8/1987 | Hruby et al. | |
| 4,853,371 A | 8/1989 | Coy et al. | |
| 7,279,298 B2 | 10/2007 | Yamaguchi et al. | |
| 8,349,576 B2 * | 1/2013 | Ryazanov | A61P 43/00 435/15 |
| 9,499,854 B2 * | 11/2016 | Parker | C12Q 1/485 |
| 10,023,902 B2 * | 7/2018 | Parker | C12Q 1/485 |
| 10,150,984 B2 * | 12/2018 | Parker | C12Q 1/485 |
| 10,266,549 B2 * | 4/2019 | Shaw | A61K 31/5383 |
| 10,590,168 B2 | 3/2020 | Parker et al. | |
| 10,648,014 B2 * | 5/2020 | Parker | C12Q 1/485 |
| 2013/0231265 A1 | 9/2013 | Parker et al. | |
| 2014/0072516 A1 | 3/2014 | Parker et al. | |
| 2016/0097084 A1 * | 4/2016 | Parker | C12Q 1/485 506/12 |
| 2016/0376632 A1 * | 12/2016 | Parker | C12Q 1/485 506/9 |
| 2017/0009273 A1 * | 1/2017 | Parker | C12Q 1/485 |
| 2018/0282372 A1 | 10/2018 | Parker et al. | |

OTHER PUBLICATIONS

Schmitz et al. Catalytic Specificity of Phosphotyrosine Kinases Blk, Lyn, c-Src and Syk as Assessed by Phage Display. J. Mol. Biol. 1996, vol. 260, pp. 664-677. (Year: 1996).*

Probst et al. Genomic resolution of a cold subsurface aquifer community provides metabolic insights for novel microbes adapted to high $CO_2$ concentrations. Environmental Microbiology, Issue Online Feb. 22, 2017, vol. 19, pp. 459-474. (Year: 2017).*

Proctor, A , et al., "Development of a peptidase-resistant substrate for single-cell measurement of protein kinase B activation", Anal Chem 84(16), 7195-7202 (2012).

Resch-Genger, U , et al., "Quantum dots versus organic dyes as fluorescent labels", Nature Methods 5(9), 763-775 (2008).

Robinson, D , et al., "The protein tyrosine kinase family of the human genome", Oncogene 19(49), 5548-5557 (2000).

Shaner, NC , et al., "Advances in fluorescent protein technology", J Cell Sci 120 (Pt 24), 4247-4260 (2007).

Sharma, V , et al., "Deep quench: an expanded dynamic range for protein kinase sensors", J Am Chem Soc 129(10), 2742-2743 (2007).

Shults, M , et al., "A multiplexed homogeneous fluorescence-based assay for protein kinase activity in cell lysates", Nature Methods 2(4), 277-283 (2005).

Smith, C , et al., "FLT3 D835 Mutations Confer Differential Resistance to Type II FLT3 Inhibitors", Leukemia 29(12), 2390-2392 (2015).

Soughayer, S , et al., "Characterization of TAT-mediated transport of detachable kinase substrates", Biochemistry 43(26), 8528-8540 (2004).

Stains, C , et al., "Interrogating signaling nodes involved in cellular transformations using kinase activity probes", Chem Biol 19(2), 210-217 (2012).

Stirewalt, D , "The role of FLT3 in haematopoietic malignancies", Nat Rev Cancer 3(9), 650-665 (2003).

Swords, R , et al., "Targeting the FMS-like tyrosine kinase 3 in acute myeloid leukemia", Leukemia 26(10), 2176-2185 (2012).

(Continued)

*Primary Examiner* — Marcela M Cordero Garcia
(74) *Attorney, Agent, or Firm* — Viksnins Harris Padys Malen LLP

(57) ABSTRACT

The invention provides kinase substrates and methods comprising their use.

25 Claims, 8 Drawing Sheets

Specification includes a Sequence Listing.

(56) References Cited

OTHER PUBLICATIONS

Tang, J , et al., "Detection of early Abl kinase activation after ionizing radiation by using a peptide biosensor", Chembiochem 13(5), 665-673 (2012).
Terai, T , et al., "Small-molecule fluorophores and fluorescent probes for bioimaging", Pflugers Arch 465, 347-359 (2013).
Tremblay, MS , et al., "Phosphorylation state-responsive lanthanide peptide conjugates: a luminescence switch based on reversible complex reorganization", Org Lett 8(13), 2723-2726 (2006).
Umezawa, K , et al., "New trends in near-infrared fluorophores for bioimaging", Analytical Sciences 30, 327-349 (2014).
Vogel, KW , et al., "Improving lanthanide-based resonance energy transfer detection by increasing donor-acceptor distances", J Biomol Screen 11, 439 (2006).
Wang, D , et al., "High-throughput Screening of Peptide Substrates for Tyrosine Kinases Featuring Precisio (tm) Kinases and Pepscreen (r) Custom Peptide Library", Sigma Aldrich sales literature, 3 pages, available May 15, 2015.
Wang, Q , et al., "Multicolor monitoring of dysregulated protein kinases in chronic myelogenous leukemia", ACS Chem Biol 5, 887-895 (2010).
White, D , et al., "Functional activity of the OCT-1 protein is predictive of long-term outcome in patients with chronic-phase chronic myeloid leukemia treated with imatinib", J Clin Oncol 28(16), 2761-2767 (2010).
Wysocki, LM , et al., "Advances in the chemistry of small molecule fluorescent probes", Current Opinion in chemical Biology 15, 752-759 (2011).
Yamamoto, Y , et al., "Activating mutation of D835 within the activation loop of FLT3 in human hematologic malignancies", Blood 97(8), 2434-2439 (2001).
Yang, T , et al., "R33CA183671: Multiplexed kinase biosensor technology to detect leukemia signaling with mass spectrometry", Poster, 17th Annual Innovative Molecular Analysis Technologies (IMAT) Principal Investigators' (PI) Meeting, Bethesada, Maryland, 4 pages (2016).
Yeh, R , et al., "Real time visualization of protein kinase activity in living cells", J Biol Chem 277(13), 11527-11532 (2002).
Yoshimoto, G , et al., "FLT3-ITD up-regulates MCL-1 to promote survival of stem cells in acute myeloid leukemia via FLT3-ITD-specific STAT5 activation", Blood 114(24), 5034-5043 (2009).
Zheng, Q , et al., "Ultra-stable organic fluorophores for single-molecule research", Chem Soc Rev 43, 1044-1056 (2014).
Akiba, H , et al., "Click conjugation of a binuclear terbium(III) complex for real-time detection of tyrosine phosphorylation", Anal Chem 87(7), 3834-3840 (2015).
Arora, A , et al., "Role of Tyrosine Kinase Inhibitors in Cancer Therapy", Journal of Pharmacology and Experimental Therapeutics 315, 971-979 (2005).
Bendall, SC , et al., "Single-cell mass cytometry of differential immune and drug responses across a human hematopoietic continuum", Science 332 (6030), 687-696 (2011).
Bohmer, F , et al., "A substrate peptide for the FLT3 receptor tyrosine kinase", Br J Haematol 144(1), 127-130 (2009).
Chozinski, TJ , et al., "Twinkle, twinkle little star: photoswitchable fluorophores for super-resolution imaging", FEBS Letters 588, 3603-3612 (2014).
Cui, W , et al., "Modular, Antibody-free Time-Resolved LRET Kinase Assay Enabled by Quantum Dots and Tb(3+)—sensitizing Peptides", Sci Rep 6, 28971, DOI: 10.1038/srep28971 (2016).
Dai, Z , et al., "Visual snapshots of intracellular kinase activity at the onset of mitosis", Chem Biol 14(11), 1254-1260 (2007).
Deng, Y , et al., "Global Analysis of Human Nonreceptor Tyrosine Kinase Specificity Using High-Density Peptide Microarrays", J Proteome Res 13(10), 4339-4346 (2014).
Ding, Y , et al., "Förster resonance energy transfer-based biosensors for multiparameter ratiometric imaging of Ca2 + dynamics and caspase-3 activity in single cells", Anal Chem 83, 9687-9693 (2011).
Enterina, Jr. , et al., "Emerging fluorescent protein technologies", Current Opinion in Chemical Biology 27, 10-17 (2015).
Galperin, E , et al., "Three-chromophore FRET microscopy to analyze multiprotein interactions in living cells", Nat Methods 1, 209-217 (2004).
Gao, X , et al., "FRET-based activity biosensors to probe compartmentalized signaling", Chembiochem 11(2), 147-151 (2010).
Genbank , "Thyroglobulin Precursor [Bos taurus]", Asscssion No. CAA26584.1, 3 pages, Apr. 18, 2005.
Ghadiali, J , et al., "Protein kinase-actuated resonance energy transfer in quantum dot—peptide conjugates", ACS Nano 4(8), 4915-4919 (2010).
Grant, D , et al., "Multiplexed FRET to image multiple signaling events in live cells", Biophysical Journal 95(10), L69-71 (2008).
Gschwind, A , et al., "The discovery of receptor tyrosine kinases: targets for cancer therapy", Nat Rev Cancer 4(5), 361-370 (2004).
Hildebrandt, N , et al., "Luminescent terbium complexes: Superior Förster resonance energy transfer donors for flexible and sensitive multiplexed biosensing", Coordination Chemistry Reviews vol. 273-274, 125-138 (2014).
Horton, RA , et al., "Multiplexing terbium- and europium-based TR-FRET readouts to increase kinase assay rapacity", J Biomol Screen 15, 1008-1015 (2010).
Hospital, M , et al., "FLT3 inhibitors: clinical potential in acute myeloid leukemia", Onco Targets Ther 10, 607-615 (2017).
Irish, J , et al., "B-cell signaling networks reveal a negative prognostic human lymphoma cell subset that emerges during tumor progression", Proc Natl Acad Sci 107(29), 12747-12754 (2010).
Irish, J , et al., "Mapping normal and cancer cell signalling networks: towards single-cell proteomics", Nat Rev Cancer 6(2), 146-155 (2006).
Kienzler, A , et al., "Novel three-color FRET tool box for advanced protein and DNA analysis", Bioconjug Chem 22, 1852-1863 (2011).
Kim, S , et al., "Monitoring a coordinated exchange process in a four-component biological interaction system: development of a time-resolved terbium-based one-donor/three-acceptor multicolor FRET system", J Am Chem Soc 132(13), 4685-4692 (2010).
Kim, Y , et al., "Quantitative fragment analysis of FLT3-ITD efficiently identifying poor prognostic group with high mutant allele burden or long ITD length", Blood Cancer Journal 5, e336, 7 pages (2015).
Kubota, K , et al., "Sensitive multiplexed analysis of kinase activities and activity-based kinase identification", Nat Biotechnol 27 (10), 933-940 (2009).
Kunz, R , et al., "A high-throughput, multiplexed kinase assay using a benchtop orbitrap mass spectrometer to investigate the effect of kinase inhibitors on kinase signaling pathways", Analytical Chemistry 84(14), 6233-6239 (2012).
Kupcho, KR , et al., "Simultaneous monitoring of discrete binding events using dual-acceptor terbium-based LRET", J Am Chem Soc 129, 13372-13373 (2007).
Kuppers, R , "Mechanisms of B-cell lymphoma pathogenesis", Nat Rev Cancer 5(4), 251-262 (2005).
Lagunas-Rangel, F , et al., "FLT3-ITD and its current role in acute myeloid leukaemia", Med Oncol 34(6), 114 (2017).
Lawrence, D , et al., "Seeing is believing: peptide-based fluorescent sensors of protein tyrosine kinase activity", Chembiochem 8(4), 373-378 (2007).
Leick, M , et al., "The Future of Targeting FLT3 Activation in AML", Curr Hematol Malig Rep 12(3), 153-167 (2017).
Leung, A , et al., "FLT3 inhibition: a moving and evolving target in acute myeloid leukaemia", Leukemia 27(2), 260-268 (2013).
Lipchik, AM , et al., "A peptide-based biosensor assay to detect intracellular Syk kinase activation and inhibition", Biochemistry 51, 7515-7524 (2012).
Lipchik, A , et al., "KINATEST-ID: a pipeline to develop phosphorylation-dependent terbium sensitizing kinase assays", J Am Chem Soc 137, 2484-2494 (2015).
Lipchik, AM , et al., "Multicolored, $Tb^{3+}$ -Based Antibody-Free Detection of Multiple Tyrosine Kinase Activities", Anal Chem 87(15), 7555-7558 (2015).

(56) References Cited

OTHER PUBLICATIONS

Lipchik, AM , et al., "Time-resolved luminescence detection of spleen tyrosine kinase activity through terbium sensitization", Anal Chem 85, 2582-2588 (2013).
Lowe, S , et al., "Multiplex sensing of protease and kinase enzyme activity via orthogonal coupling of quantum dot-peptide conjugates", ACS Nano 6(1), 851-857 (2012).
Lukovic, E , et al., "Recognition-domain focused chemosensors: versatile and efficient reporters of protein kinase activity", J Am Chem Soc 130(38), 12821-12827 (2008).
Marholz, L , et al., "In Silico Design and in Vitro Characterization of Universal Tyrosine Kinase Peptide Substrates", Biochemistry 57(12), 1847-1851 (2018).
Mashinchian , "Impacts of quantum dots in molecular detection and bioimaging of cancer.", BioImpacts 4, 149-166 (2014).
Mercken, L , et al., "Primary Structure of bovine thyroglobulin deduced from the sequence of its 8,431-base complementary DNA", Nature 316, 647-651 (1985).
Meredith, G , et al., "Measurement of kinase activation in single mammalian cells", Nat Biotechnol 18(3), 309-312 (2000).
Ni, Q , et al., "Dynamic visualization of cellular signaling", Advanced in Biochemical Eng Botechnol 119, 79-97 (2010).
Olenych, SG , et al., "The fluorescent protein color palette", Curr Protoc Cell Biol, Chapter 21, Unit 21.5 (2007).
Parker, L , "Multiplexed Kinase Biosensor Technology to Detect Leukemia Signaling with Mass Spectrometry", 17th Annual Innovative Molecular Analysis Technologies (IMAT) Principal Investigators' (PI) Meeting, Bethesada, Maryland, pp. 1-19 and 157-158 (2016).
Perez, M , et al., "Identification of FMS-Like Tyrosine Kinase 3 (FLT3) Substrates Using KALIP", Poster 63, United States Human Proteome Organization (US-HUPO) Conference, San Diego, CA, 7 pages (Mar. 2017).
Peyker, A , et al., "Imaging activation of two Ras isoforms simultaneously in a single cell", Chembiochem 6, 78-85 (2005).
Piljic, A , et al., "Simultaneous recording of multiple cellular events by FRET", ACS Chem Biol 3(3), 156-160 (2008).
Placzek, E , et al., "A peptide biosensor for detecting intracellular Abl kinase activity using matrix-assisted laser desorption/ionization time-of-flight mass spectrometry", Anal Biochem 397(1), 73-78 (2010).
Pozarowski, P , et al., "Analysis of cell cycle by flow cytometry", Methods Mol Biol 281, 301-311 (2004).

\* cited by examiner

FIGURES 1A-B

**Common motifs defined for each *in silico* library**

| Position | -4 | -3 | -2 | -1 | 0 | 1 | 2 | 3 | 4 |
|---|---|---|---|---|---|---|---|---|---|
| library 1 | E D S P | D E N G K S | D G N E P Q | I V D E F P | Y | D E S G | S N D E F Q T G | V P I L M S | D R E P |
| library 2 | E | D | P D G N E | D E F I P | Y | D E V I | T S N D E | V P L M S | E |

A

FIGURES 3B-C
B
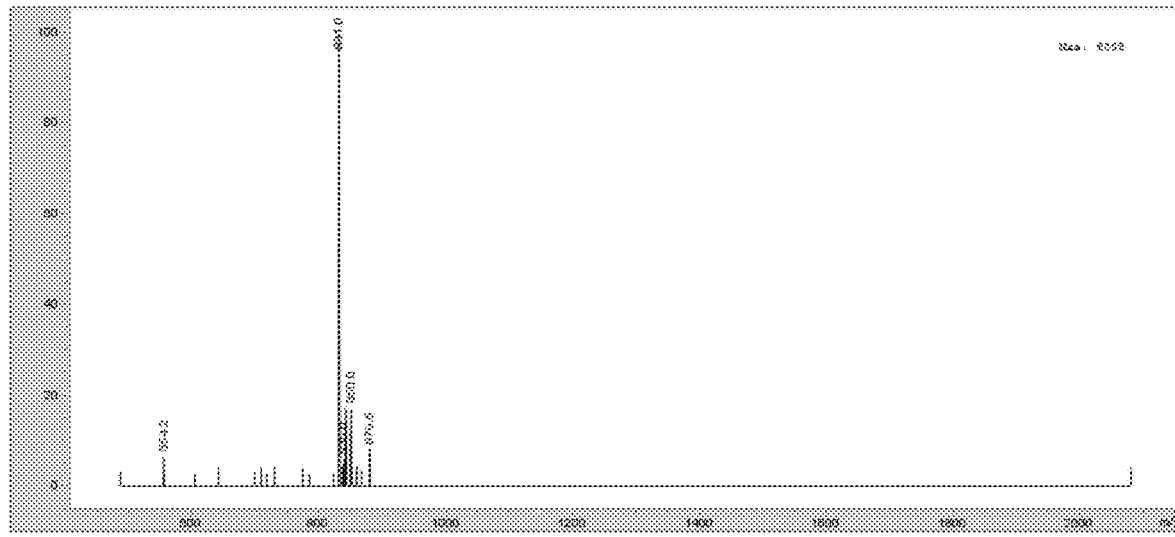
C
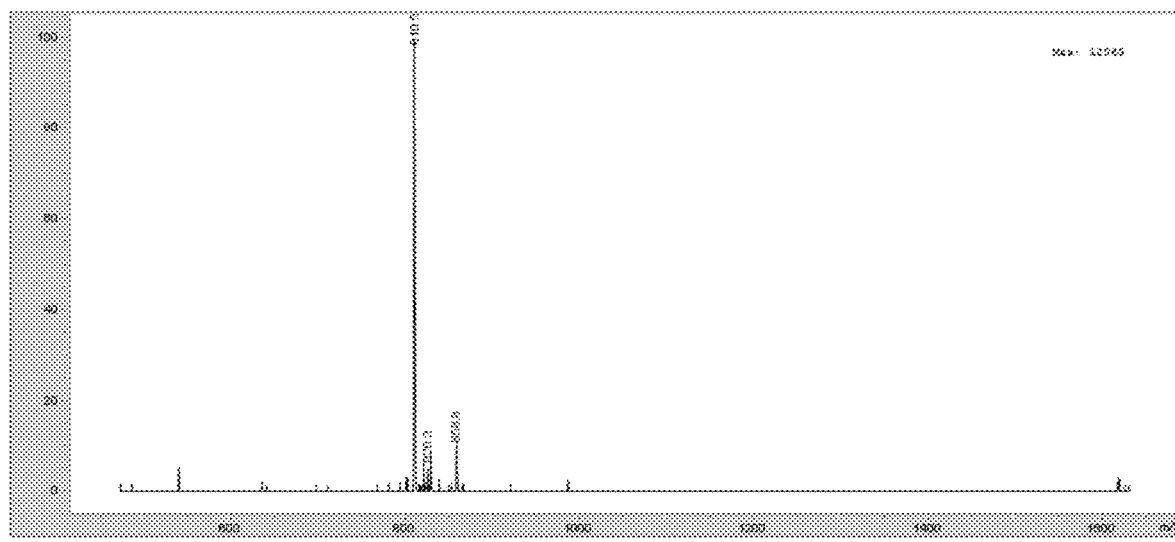

FIGURES 3D-E
D
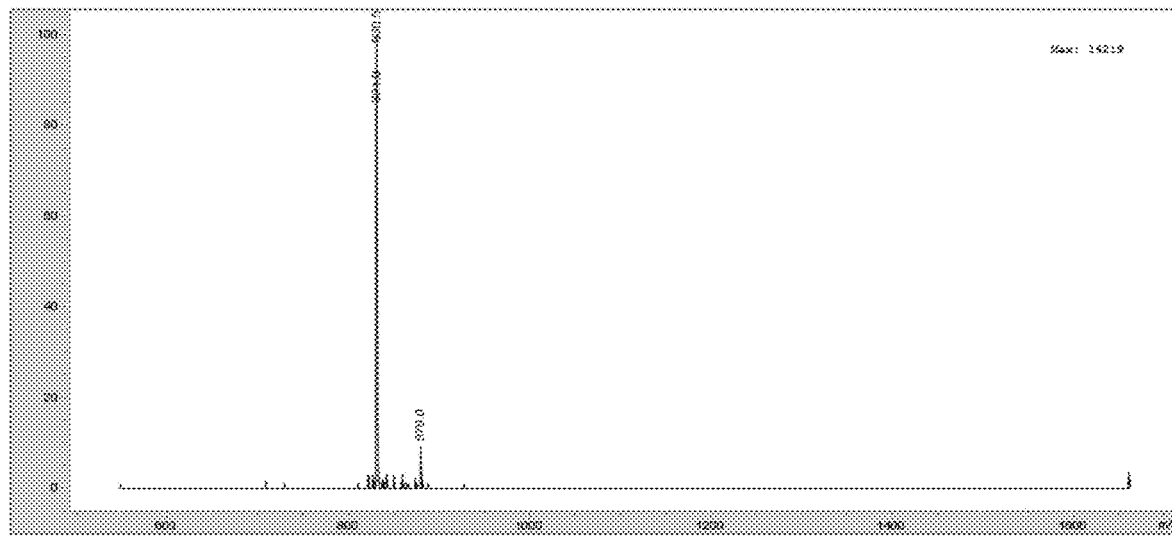
E
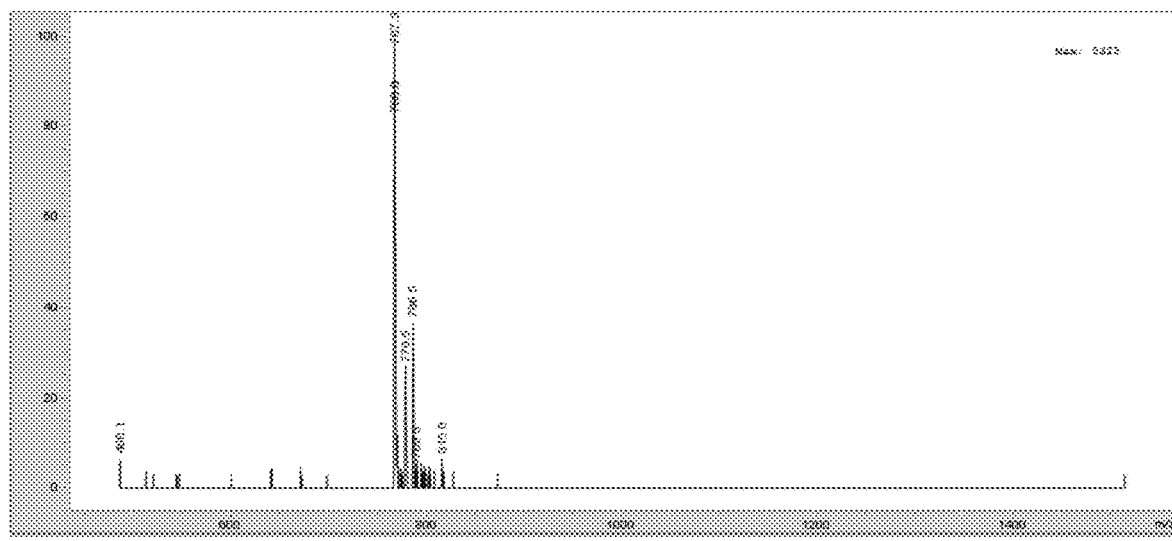

FIGURES 3F-G
F
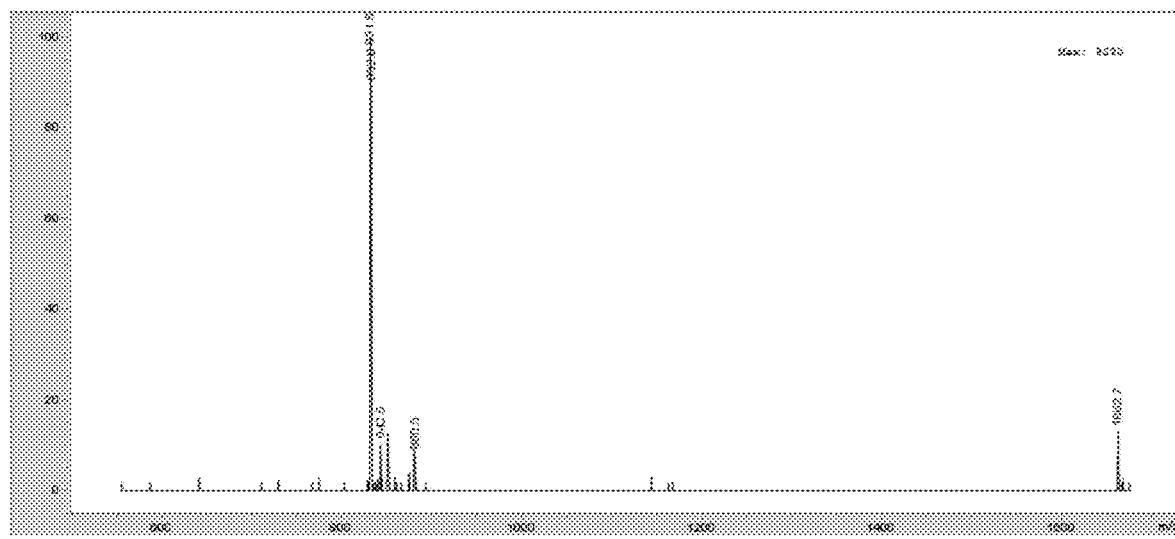
G
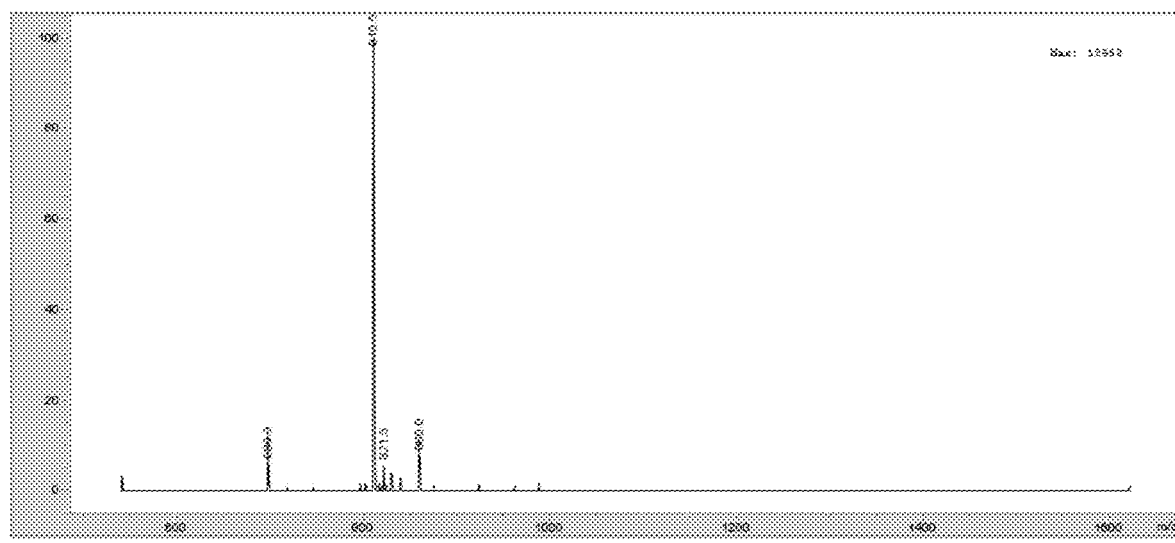

FIGURES 3H-I
H
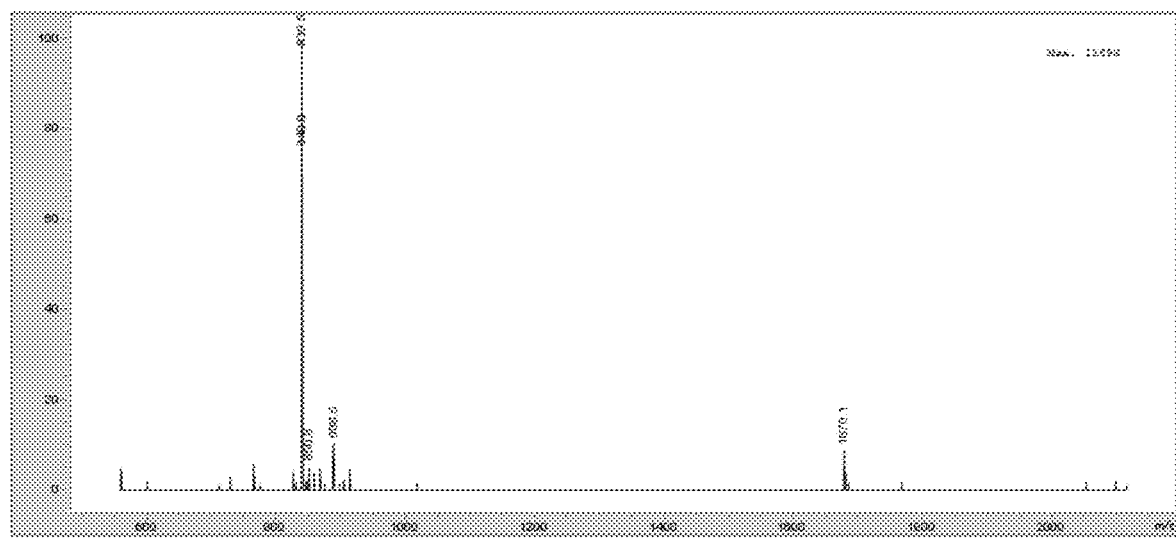
I
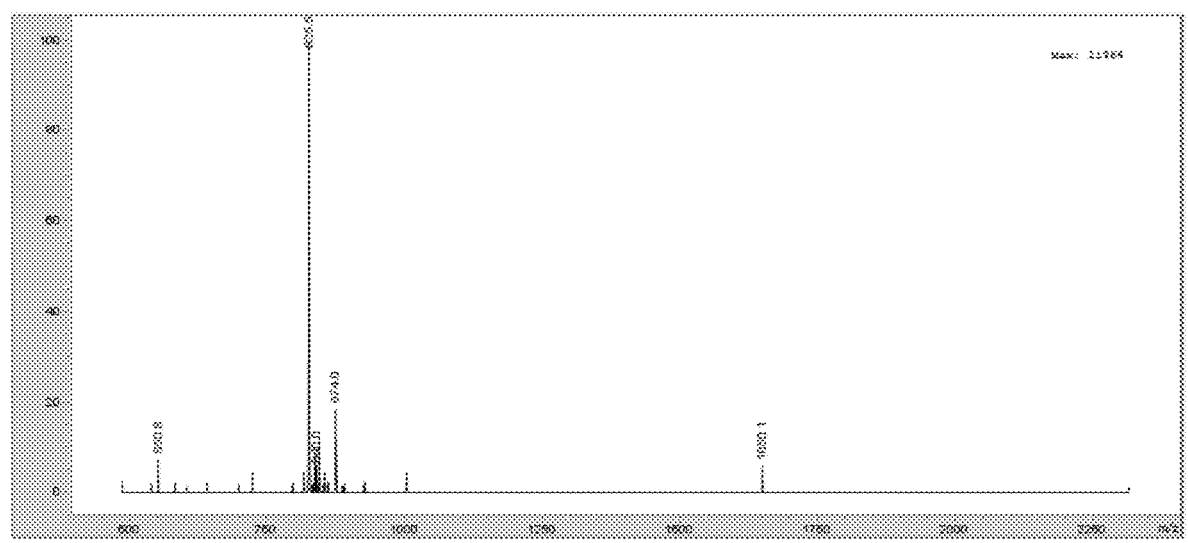

FIGURES 3J-K
J
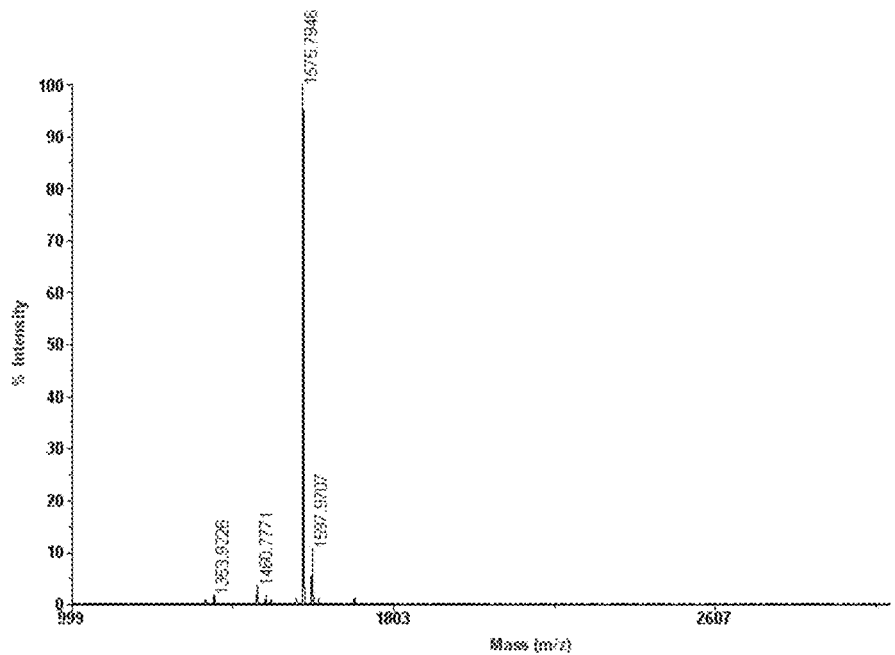
K
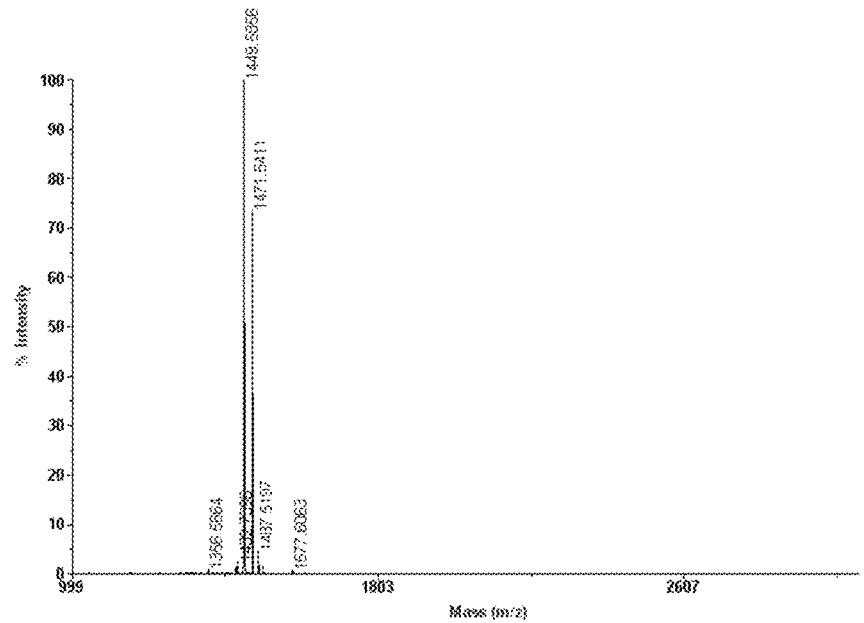

UNIVERSAL KINASE SUBSTRATES AND METHODS OF USE THEREOF

RELATED APPLICATION

This application claims the benefit of priority of U.S. Provisional Application Ser. No. 62/633,997 filed on Feb. 22, 2018, which application is incorporated by reference herein.

SEQUENCE LISTING

The instant application contains a Sequence Listing which has been filed electronically in ASCII format and is hereby incorporated by reference in its entirety. Said ASCII copy, created on May 2, 2019, is named 09531_450US1_SL.txt and is 6,901 bytes in size.

GOVERNMENT FUNDING

This invention was made with government support under R33CA183671 and R01CA182543 awarded by the National Institutes of Health and the National Cancer Institute. The government has certain rights in this invention.

BACKGROUND

Protein tyrosine kinases (PTKs) are responsible for phosphorylating specific tyrosine residues in substrate proteins, which can regulate a variety of cellular signaling pathways. This post-translational covalent modification can affect the activity, subcellular localization, or stability of proteins thereby modulating critical processes ranging from cell growth and proliferation, metabolism, differentiation, and migration (Gschwind, et al., Nature Reviews Cancer 2004, 4, nrc1360). Because deregulation of these processes are key events in cancer progression, PTKs have emerged as important drug targets, with many PTK inhibitors in current clinical use as cancer therapeutics (Arora, A.; Scholar, E. M. Journal of Pharmacology and Experimental Therapeutics 2005, 315, 971). One of the key ways to identify small molecule PTK inhibitors is through activity-based screens that assay phosphorylation of a substrate in the presence of the compound. For well-studied kinases, efficient peptide or protein substrates are known for use in these assays. However, availability of assays for the "orphan" kinome is less straightforward. Of the 90 receptor and non-receptor tyrosine kinases encoded in the human genome (Robinson, et al., Oncogene 2000, 19, 1203957), up to 90% are relatively understudied with few high-quality substrates identified.

In the absence of an established substrate, a common approach these kinases is to use sequences containing tyrosine and various molar ratios of glutamic acid residues (polyGlu-Tyr) either as a homogenous sequence (e.g. EEEEYEEEE (SEQ ID NO: 23)), or more commonly, as a heterogeneous polymeric material. These substrates are commercially available and often included in PTK assay kits, and have subsequently been used for decades in widespread applications to evaluate activity and to serve as pseudo-universal substrates in tyrosine kinase assays (Ali, et al., Journal of Biological Chemistry 1994, 269, 31626; Blouin, et al., Current Chemical Genomics 2011, 5, 115; Rebas, et al., Medical Science Monitor, 7, BR884; Varkondi, et al., Journal of Receptor and Signal Transduction Research 2005, 25, 45; Hayashi, et al., J Blol Chem 1987, 262, 16692; Varkondi, et al., J Recept Signal Transduct Res 2005, 25, 45). Because PTKs often have strict substrate specificity, random mixtures of polyGlu-Tyr peptides are usually phosphorylated inefficiently, often to low stoichiometry (Rijksen, et al., Breast Cancer Research and Treatment 1996, 39, 139). Due to the heterogeneous nature of the polymer, the same sample may contain components that a given kinase will phosphorylate, but may also harbor sequences that act as inhibitors of enzymatic activity. This inconsistency impedes accurate comparison of activity between preparations of substrate and across different assay conditions. Also, these heterogeneous polymers are not compatible with high-throughput assays commonly employed for inhibitor screening (e.g. LanthaScreen or AlphaScreen technologies and other TR-FRET applications), making it very challenging to develop new, efficient assays to target understudied kinases. Further, comparing relative activity of the same or different kinases from multiple preparations or assays is a poorly recognized, confounding challenge in drug screening.

Thus, there is a need for new compounds and compositions to study PTKs. Specifically, there is a need for universal substrates that may be used to evaluate the activity of PTKs.

SUMMARY OF THE INVENTION

Thus, certain embodiments of the invention provide a peptide that may be used as a substrate for a plurality of PTKs (e.g., 2, 3, 4, 5, 6, 7, 8, 9, 10 or more PTKs). Such "universal substrates" could enable assay standardization by calibrating specific activity between batches of enzyme and assay replicates. Additionally, having a standardized substrate for screening would facilitate kinome-wide profiling of inhibitor specificity, which is important for assessment of potential off-target activity. As described herein, these peptides were designed using the KINATEST-ID platform.

Accordingly, certain embodiments of the invention provide a peptide comprising a first amino acid sequence having at least about 80% sequence identity to an amino acid sequence of formula I:

$$R^{1a}-R^{2a}-R^{3a}-R^{4a}-R^{5a}-R^{6a}-R^{7a}-R^{8a}-R^{9a} \tag{I}$$

wherein:

$R^{1a}$ is selected from the group consisting of: E, D, S and P;

$R^{2a}$ is selected from the group consisting of: D, E, N, G, K and S;

$R^{3a}$ is D, G, N, E, Q, P and A;

$R^{4a}$ is selected from the group consisting of: I, V, D, E, F and P;

$R^{5a}$ is Y;

$R^{6a}$ is selected from the group consisting of: D, E, S, G, I, V and A;

$R^{7a}$ is S, N, D, E, F, Q, G and T;

$R^{8a}$ is selected from the group consisting of: P, I, M, S, L, V; and $R^{9a}$ is selected form the group consisting of: D, R, P, E and A;

or a salt thereof.

Certain embodiments of the invention provide a peptide comprising a first amino acid sequence having at least about 80% sequence identity to an amino acid sequence of formula Ia:

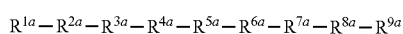

$$R^{1a}-R^{2a}-R^{3a}-R^{4a}-R^{5a}-R^{6a}-R^{7a}-R^{8a}-R^{9a} \quad \text{(Ia)}$$

wherein:
  $R^{1a}$ is selected from the group consisting of: E, D;
  $R^{2a}$ is selected from the group consisting of: D, E;
  $R^{3a}$ is P, A;
  $R^{4a}$ is selected from the group consisting of: I;
  $R^{5a}$ is Y;
  $R^{6a}$ is selected from the group consisting of: V, A;
  $R^{7a}$ is T;
  $R^{8a}$ is selected from the group consisting of: L, V; and
  $R^{9a}$ is selected form the group consisting of: E, A;
  or a salt thereof.

Certain embodiments of the invention provide a peptide comprising a first amino acid sequence having at least about 80% sequence identity to EDDVYDSVP (SEQ ID NO:7).

Certain embodiments of the invention provide a method for detecting phosphorylation activity of a kinase, comprising:
  1) contacting the kinase with a peptide as described herein to provide a resulting mixture;
  2) measuring a signal from a detectable agent; and
  3) detecting phosphorylation activity of the kinase when changes in the signal are detected as compared to a control.

Certain embodiments of the invention provide a method for detecting phosphorylation activity of a kinase, comprising:
  1) contacting the kinase with a test peptide to provide a first resulting mixture;
  2) measuring a signal from a detectable agent in the first resulting mixture;
  3) contacting the kinase with a peptide as described herein to provide a second resulting mixture;
  4) measuring a signal from a detectable agent in the second resulting mixture; and
  5) standardizing the signal from the first resulting mixture using the signal measurements from the second resulting mixture; and
  6) detecting phosphorylation activity of the kinase when the standardized signal from the first resulting mixture is above a reference value.

Certain embodiments of the invention provide a method for identifying a substrate of a kinase, comprising:
  1) contacting the kinase with a test peptide to provide a first resulting mixture;
  2) measuring a signal from a detectable agent in the first resulting mixture;
  3) contacting the kinase with a peptide as described herein to provide a second resulting mixture;
  4) measuring a signal from a detectable agent in the second resulting mixture; and
  5) standardizing the signal from the first resulting mixture using the signal measurements from the second resulting mixture; and
  6) identifying the test peptide as a substrate of the kinase when the standardized signal from the first resulting mixture is above a reference value.

Certain embodiments of the invention provide a method to identity an inhibitor of a kinase comprising:
  1) contacting a peptide as described herein, the kinase and a test compound to provide a resulting mixture;
  2) measuring a signal from a detectable agent in the resulting mixture; and
  3) identifying the test compound as an inhibitor of the kinase when changes in the signal are detected as compared to a control.

Certain embodiments of the invention provide a method to identity an inhibitor of a kinase comprising:
  1) contacting a peptide as described herein and the kinase to provide a first resulting mixture;
  2) measuring a signal from a detectable agent in the first resulting mixture;
  3) contacting a peptide as described herein, the kinase and a test compound to provide a second resulting mixture;
  4) measuring a signal from a detectable agent in the second resulting mixture; and
  5) identifying the test compound as an inhibitor of the kinase when changes between the signal in the first resulting mixture and the signal from the second resulting mixture are detected.

Certain embodiments of the invention provide a method to design a peptide substrate which detects the activity of a plurality of protein tyrosine kinases (PTKs) comprising:
  1) generating a candidate set of peptide substrates comprising the peptides as described herein;
  2) excluding one or more peptides from the candidate set, which are likely to not be phosphorylated by a plurality of kinases; and
  3) screening the remaining peptides from step 2) for the ability to act as a substrate for a plurality of kinases.

Certain embodiments of the invention provide a method to design a peptide substrate which detects the activity of a plurality of protein tyrosine kinases (PTKs) comprising:
  1) analyzing the amino acid preference profiles for a panel of PTKs using the KINATEST_ID algorithm to generate a candidate set of peptide substrates;
  2) excluding one or more peptides from the candidate set, which are likely to not be phosphorylated by a plurality of kinases; and
  3) screening the remaining peptides from step 2) for the ability to act as a substrate for a plurality of kinases.

The invention also provides processes and intermediates disclosed herein that are useful for preparing a peptide as described herein, or a salt thereof.

BRIEF DESCRIPTION OF THE FIGURES

FIG. 1A) Initial screen of the pilot library to test substrate suitability against a panel of 15 PTKs. FIG. 1B) Peptides 2 and 5 had the highest phosphorylation averaged across the kinase panel (each point is an individual kinase, lines show mean and 95% confidence interval) and were therefore designated universal substrate hits. Consensus peptides reported previously for the respective kinases (labeled "ACK, LYN, BMX, SYK, CSK and ABL" in both panels) were used controls (Deng, et al., *Journal of Proteome Research* 2014, 13, 4339).

FIG. 2. The amino acids and their positions used to generate library 1 and library 2.

FIGS. 3A-K. The characterization data for the nine purified peptides (1-9) in the pilot library and the purified peptides used for the kinetic characterization experiments (10-11) is shown. FIG. 3A. Peptide 1: sequence EDDEYVT-PEGGK$_{biotin}$GG (SEQ ID NO: 10), m/z calcd for $C_{70}H_{104}N_{18}O_{28}S$ $[M+2H]^{2+}$ 839.4, found 839.5. FIG. 3B. Peptide 2: sequence EDPIYVTLEGGK$_{biotin}$GG (SEQ ID NO: 11), m/z calcd for $C_{73}H_{114}N_{18}O_{24}S$ $[M+2H]^{2+}$ 830.4, found 831.0. FIG. 3C. Peptide 3: sequence DEDIYGT- PEGGK$_{biotin}$GG (SEQ ID NO: 12), m/z calcd for C$_{68}$H$_{102}$N$_{18}$O$_{26}$S [M+2H]$^{2+}$ 810.3, found 810.5. FIG. 3D. Peptide 4: sequence DEPIYDTPEGGK$_{biotin}$GG (SEQ ID NO: 13), m/z calcd for C$_{71}$H$_{106}$N$_{18}$O$_{26}$S [M+2H]$^{2+}$ 830.4, found 830.5. FIG. 3E. Peptide 5: sequence DEAIYATVAGGK$_{biotin}$GG (SEQ ID NO: 14), m/z calcd for C$_{66}$H$_{104}$N$_{18}$O$_{22}$S [M+2H]$^{2+}$ 767.4, found 767.3. FIG. 3F. Peptide 6: sequence DEPIYDTVEGGK$_{biotin}$GG (SEQ ID NO:15), m/z calcd for C$_{71}$H$_{108}$N$_{18}$O$_{26}$S [M+2H]$^{2+}$ 831.4, found 831.5. FIG. 3G. Peptide 7: sequence EDDVYDSVPGGK$_{biotin}$GG (SEQ ID NO: 16), m/z calcd for C$_{68}$H$_{102}$N$_{18}$O$_{26}$S [M+2H]$^{2+}$ 810.3, found 810.5. FIG. 3H. Peptide 8: sequence EDDEYISPEGGK$_{biotin}$GG (SEQ ID NO: 17), m/z calcd for C$_{70}$H$_{104}$N$_{18}$O$_{28}$S [M+2H]$^{2+}$ 839.4, found 839.5. FIG. 3I. Peptide 9: sequence EDDEYATPEGGK$_{biotin}$GG (SEQ ID NO: 18), m/z calcd for C$_{68}$H$_{100}$N$_{18}$O$_{28}$S [M+2H]$^{2+}$ 825.3, found 825.5. FIG. 3J. Peptide 10: sequence EDPIYVTLEGGKKK (SEQ ID NO:19), m/z calcd for C$_{71}$H$_{118}$N$_{18}$O$_{22}$ [M+H]$^{+}$ 1575.87, found 1575.7946. FIG. 3K. Peptide 11: sequence DEAIYATVAGGKKK (SEQ ID NO:20), m/z calcd for C$_{64}$H$_{108}$N$_{18}$O$_{20}$ [M+H]$^{+}$ 1449.80, found 1449.5856.

DETAILED DESCRIPTION

Figure 1:
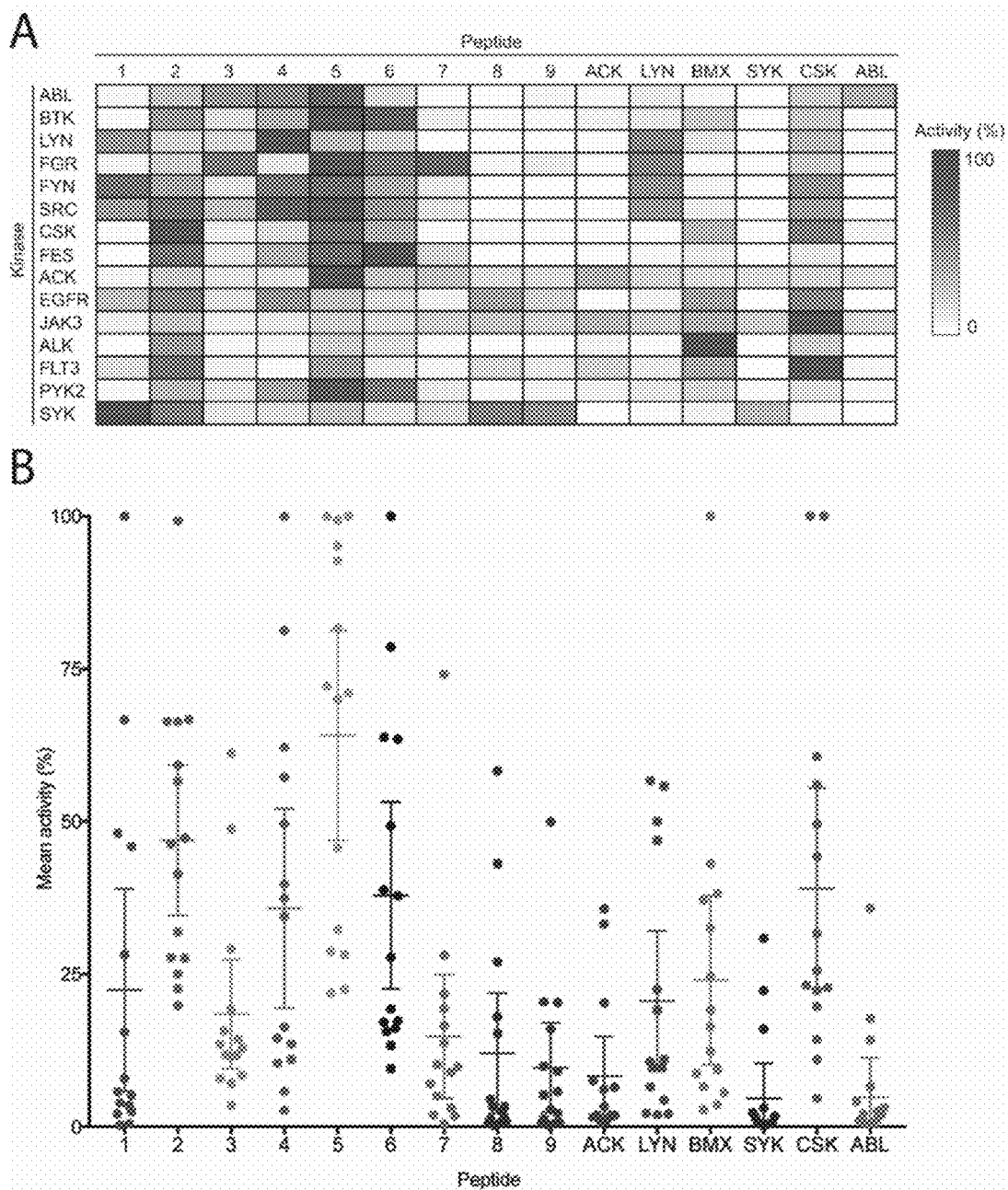
FIGS. 1A-B.

Kinase enzyme preparations are notoriously difficult to standardize for functional activity. From one recombinant preparation or lysate preparation to another, the enzyme may have different intrinsic activity levels despite containing the same amount of enzyme protein. Therefore, from one preparation to another it is very difficult to compare the levels of phosphorylation of a range of substrates (artificial or natural). Furthermore, it is nearly impossible to reliably compare the activity of a range of kinases on the same substrate, because of this same variability in intrinsic activity from preparation to preparation and enzyme to enzyme. Currently, some chosen specific peptide or a heterogeneous preparation of poly-glutamic acid-tyrosine (polyGluTyr) is often used for quality control of an enzyme preparation even if it is not optimal or efficient for the enzyme of interest. This means the activity levels seen can be irrelevant to other more optimal substrates.

Accordingly, described herein is the development of nonselective, optimized "universal" tyrosine kinase substrates that may be used, e.g., as activity normalizers for any kinase of interest. For example, these universal kinase substrates can be characterized for their specific activity levels with individual kinases and then used as "standardizers" for intrinsic activity for quality control and normalization of kinase enzyme preparations for comparative experiments. As described herein, these peptides may be rationally designed through a bioinformatics approach, which transforms an input library of verified substrate sequences to an output set of specific candidate biosensor sequences based on a statistical analysis of amino acid preferences at positions neighboring the phosphosite.

Thus, certain embodiments of the invention provide a peptide that is a substrate for two or more PTKs (e.g., 2, 3, 4, 5, 6, 7, 8, 9, 10, 15, 20, 25, 30, 35, 40, 45, 50, 55, 60, 65, 70, 75, 80, 85 or more PTKs). In certain embodiments, the peptide is a substrate for two or more PTKs described herein (e.g., 2, 3, 4, 5, 6, 7, 8, 9, 10, 15, 20, 25, 30, 35, 40, 45, 50, 55, 60, 65, 70, 75, 80, 85 or more PTKs described herein) (e.g., in the Examples and Figures). In certain embodiments, the peptide is a substrate for two or more receptor tyrosine kinases (RTKs). In certain embodiments, the peptide is a substrate for two or more non-receptor tyrosine kinases (NRTKs). In certain embodiments, the peptide is a substrate for at least one RTK and at least one NRTK.

In certain embodiments, the peptide is a substrate for two or more PTKs selected from the group consisting of AATK, ABL, ABL2, ACK, ALK, ARG, AXL, BLK, BMX, BTK, CSF1R, CSK, DDR1, DDR2, EGFR, EPHA1, EPHA2, EPHA3, EPHA4, EPHA5, EPHA6, EPHA7, EPHA8, EPHA10, EPHB1, EPHB2, EPHB3, EPHB4, EPHB6, ERBB2, ERBB3, ERBB4, FER, FES, FGFR1, FGFR2, FGFR3, FGFR4, FGR, FLT1, FLT3, FLT4, FRK, FYN, GSG2, HCK, IGF1R, ILK, INSR, INSRR, IRAK4, ITK, JAK1, JAK2, JAK3, KDR, KIT, KSR1, LCK, LMTK2, LMTK3, LTK, LYN, MATK, MERTK, MET, MLTK, MST1R, MUSK, NPR1, NTRK1, NTRK2, NTRK3, PDGFRA, PDGFRB, PLK4, PTK2, PTK2B, PTK6, PTK7, PYK2, RET, ROR1, ROR2, ROS1, RYK, SGK493, SRC, SRMS, STYK1, SYK, TEC, TEK, TEX14, TIE1, TNK1, TNK2, TNNI3K, TXK, TYK2, TYRO3, YES1 and ZAP70.

In certain embodiments, the peptide is a substrate for two or more PTKs selected from the group consisting of AATK, ABL, ABL2, ACK, ALK, ARG, AXL, BLK, BMX, BTK, BRK, CSF1R, CSK, DDR1, DDR2, EGFR, EPHA1, EPHA2, EPHA3, EPHA4, EPHA5, EPHA6, EPHA7, EPHA8, EPHA10, EPHB1, EPHB2, EPHB3, EPHB4, EPHB6, ERBB2, ERBB3, ERBB4, FER, FES, FGFR1, FGFR2, FGFR3, FGFR4, FGR, FLT1, FLT3, FLT4, FMS, FRK, FYN, GSG2, HCK, IGF1R, ILK, INSR, INSRR, IR, IRAK4, ITK, JAK1, JAK2, JAK3, KDR, KIT (c-KIT), KSR1, LCK, LMTK2, LMTK3, LTK, LYN, MATK, c-MER, MERTK, MET (c-MET), MLTK, MST1R, MUSK, NPR1, NTRK1, NTRK2, NTRK3, PDGFRA, PDGFRB, PDK1/PDHK1, PDK2/PDHK2, PLK4, PTK2, PTK2B, PTK6, PTK7, PYK2, RET, ROR1, ROR2, ROS1, RYK, SGK493, SRC (c-Src), SRMS, STYK1, SYK, TEC, TEK, TEX14, TIE1, TNK1, TNK2, TNNI3K, TRKA, TRKB, TRPM7/CHAK1, TXK, TYK2, TYRO3, YES1 and ZAP70.

In certain embodiments, the peptide is a substrate for 10 or more PTKs selected from the group consisting of AATK, ABL, ABL2, ACK, ALK, ARG, AXL, BLK, BMX, BTK, BRK, CSF1R, CSK, DDR1, DDR2, EGFR, EPHA1, EPHA2, EPHA3, EPHA4, EPHA5, EPHA6, EPHA7, EPHA8, EPHA10, EPHB1, EPHB2, EPHB3, EPHB4, EPHB6, ERBB2, ERBB3, ERBB4, FER, FES, FGFR1, FGFR2, FGFR3, FGFR4, FGR, FLT1, FLT3, FLT4, FMS, FRK, FYN, GSG2, HCK, IGF1R, ILK, INSR, INSRR, IR, IRAK4, ITK, JAK1, JAK2, JAK3, KDR, KIT (c-KIT), KSR1, LCK, LMTK2, LMTK3, LTK, LYN, MATK, c-MER, MERTK, MET (c-MET), MLTK, MST1R, MUSK, NPR1, NTRK1, NTRK2, NTRK3, PDGFRA, PDGFRB, PDK1/PDHK1, PDK2/PDHK2, PLK4, PTK2, PTK2B, PTK6, PTK7, PYK2, RET, ROR1, ROR2, ROS1, RYK, SGK493, SRC (c-Src), SRMS, STYK1, SYK, TEC, TEK, TEX14, TIE1, TNK1, TNK2, TNNI3K, TRKA, TRKB, TRPM7/CHAK1, TXK, TYK2, TYRO3, YES1 and ZAP70.

In certain embodiments, the peptide is a substrate for 20 or more PTKs selected from the group consisting of AATK, ABL, ABL2, ACK, ALK, ARG, AXL, BLK, BMX, BTK, BRK, CSF1R, CSK, DDR1, DDR2, EGFR, EPHA1, EPHA2, EPHA3, EPHA4, EPHA5, EPHA6, EPHA7, EPHA8, EPHA10, EPHB1, EPHB2, EPHB3, EPHB4, EPHB6, ERBB2, ERBB3, ERBB4, FER, FES, FGFR1, FGFR2, FGFR3, FGFR4, FGR, FLT1, FLT3, FLT4, FMS, FRK, FYN, GSG2, HCK, IGF1R, ILK, INSR, INSRR, IR, IRAK4, ITK, JAK1, JAK2, JAK3, KDR, KIT (c-KIT), KSR1, LCK, LMTK2, LMTK3, LTK, LYN, MATK, c-MER, MERTK, MET (c-MET), MLTK, MST1R, MUSK, NPR1, NTRK1, NTRK2, NTRK3, PDGFRA, PDGFRB, PDK1/PDHK1, PDK2/PDHK2, PLK4, PTK2, PTK2B, PTK6, PTK7, PYK2, RET, ROR1, ROR2, ROS1, RYK, SGK493, SRC (c-Src), SRMS, STYK1, SYK, TEC, TEK, TEX14, TIE1, TNK1, TNK2, TNNI3K, TRKA, TRKB, TRPM7/CHAK1, TXK, TYK2, TYRO3, YES1 and ZAP70.

In certain embodiments, the peptide is a substrate for 40 or more PTKs selected from the group consisting of AATK, ABL, ABL2, ACK, ALK, ARG, AXL, BLK, BMX, BTK, BRK, CSF1R, CSK, DDR1, DDR2, EGFR, EPHA1, EPHA2, EPHA3, EPHA4, EPHA5, EPHA6, EPHA7, EPHA8, EPHA10, EPHB1, EPHB2, EPHB3, EPHB4, EPHB6, ERBB2, ERBB3, ERBB4, FER, FES, FGFR1, FGFR2, FGFR3, FGFR4, FGR, FLT1, FLT3, FLT4, FMS, FRK, FYN, GSG2, HCK, IGF1R, ILK, INSR, INSRR, IR, IRAK4, ITK, JAK1, JAK2, JAK3, KDR, KIT (c-KIT), KSR1, LCK, LMTK2, LMTK3, LTK, LYN, MATK, c-MER, MERTK, MET (c-MET), MLTK, MST1R, MUSK, NPR1, NTRK1, NTRK2, NTRK3, PDGFRA, PDGFRB, PDK1/PDHK1, PDK2/PDHK2, PLK4, PTK2, PTK2B, PTK6, PTK7, PYK2, RET, ROR1, ROR2, ROS1, RYK, SGK493, SRC (c-Src), SRMS, STYK1, SYK, TEC, TEK, TEX14, TIE1, TNK1, TNK2, TNNI3K, TRKA, TRKB, TRPM7/CHAK1, TXK, TYK2, TYRO3, YES1 and ZAP70.

In certain embodiments, the peptide is a substrate for 10 or more PTKs selected from the group consisting of ABL, BTK, LYN, FGR, FYN, SRC, CSK, FES, ACK, EGFR, JAK3, ALK, FLT3, PYK2 and SYK. In certain embodiments, the peptide is a substrate for ABL, BTK, LYN, FGR, FYN, SRC, CSK, FES, ACK, EGFR, JAK3, ALK, FLT3, PYK2 and SYK.

Peptides Comprising Formula I—Universal Kinase Substrates

Accordingly, certain embodiments of the invention provide a peptide comprising a first amino acid sequence having at least about 80% sequence identity to an amino acid sequence of formula I:

$$R^{1a} - R^{2a} - R^{3a} - R^{4a} - R^{5a} - R^{6a} - R^{7a} - R^{8a} - R^{9a} \quad (I)$$

wherein:
$R^{1a}$ is selected from the group consisting of: E, D, S and P;
$R^{2a}$ is selected from the group consisting of: D, E, N, G, K and S;
$R^{3a}$ is D, G, N, E, Q, P and A;
$R^{4a}$ is selected from the group consisting of: I, V, D, E, F and P;
$R^{5a}$ is Y;
$R^{6a}$ is selected from the group consisting of: D, E, S, G, I, V and A;
$R^{7a}$ is S, N, D, E, F, Q, G and T;
$R^{8a}$ is selected from the group consisting of: P, I, M, S, L, V; and
$R^{9a}$ is selected form the group consisting of: D, R, P, E and A;
or a salt thereof.

In certain embodiments, the peptide comprises a first amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% sequence identity to an amino acid sequence of formula I.

In certain embodiments, the peptide consists of a first amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% sequence identity to an amino acid sequence of formula I.

In certain embodiments, the peptide comprises a first amino acid sequence having at least about 80% sequence identity to an amino acid sequence of formula Ia:

$$R^{1a} - R^{2a} - R^{3a} - R^{4a} - R^{5a} - R^{6a} - R^{7a} - R^{8a} - R^{9a} \quad (Ia)$$

wherein:
$R^{1a}$ is selected from the group consisting of: E, D;
$R^{2a}$ is selected from the group consisting of: D, E;
$R^{3a}$ is P, A;
$R^{4a}$ is selected from the group consisting of: I;
$R^{5a}$ is Y;
$R^{6a}$ is selected from the group consisting of: V, A;
$R^{7a}$ is T;
$R^{8a}$ is selected from the group consisting of: L, V; and
$R^{9a}$ is selected form the group consisting of: E, A;
or a salt thereof.

In certain embodiments, the peptide comprises a first amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% sequence identity to an amino acid sequence of formula Ia.

In certain embodiments, the peptide consists of a first amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% sequence identity to an amino acid sequence of formula Ia.

In certain embodiments, the peptide comprises a first amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% sequence identity to EDPIYVTLE (SEQ ID NO:2).

In certain embodiments, the peptide consists of a first amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% sequence identity to EDPIYVTLE (SEQ ID NO:2).

In certain embodiments, the peptide comprises a first amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% sequence identity to DEAIYATVA (SEQ ID NO:5).

In certain embodiments, the peptide consists of a first amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% sequence identity to DEAIYATVA (SEQ ID NO:5).

FGR Peptide Substrates

Certain embodiments of the invention also provide peptides that are substrates of FGR. In certain embodiments, such a peptide comprises a first amino acid sequence having at least 80% sequence identity to SEQ ID NO:7, as described below.

Thus, certain embodiments of the invention provide a peptide comprising a first amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% sequence identity to EDDVYDSVP (SEQ ID NO:7).

In certain embodiments, the peptide consists of a first amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% sequence identity to EDDVYDSVP (SEQ ID NO:7).

Certain Embodiments of Peptides of the Invention

The peptide sequences identified and described herein can be prepared using standard techniques.

Typically, a peptide of the invention is about 6 to about 15 amino acids in length. For example, in certain embodiments, the peptide is 9 amino acids in length. However, the length of the peptide is not critical, provided it can act as a substrate for the kinase, and as such, may be longer or shorter. Accordingly, in certain embodiments, the peptide is about 5 to about 1000 amino acids in length. In certain embodiments, the peptide is about 5 to about 500 amino acids in length. In certain embodiments, the peptide is about 5 to about 250 amino acids in length. In certain embodiments, the peptide is about 5 to about 150 amino acids in length. In certain embodiments, the peptide is about 5 to about 100 amino acids in length. In certain embodiments, the peptide is about 5 to about 75 amino acids in length. In certain embodiments, the peptide is about 5 to about 75 amino acids in length. In certain embodiments, the peptide is about 5 to about 50 amino acids in length. In certain embodiments, the peptide is about 6 to about 50 amino acids in length. In certain embodiments, the peptide is about 5 to about 25 amino acids in length. In certain embodiments, the peptide is about 5 to about 20 amino acids in length.

In certain embodiments, a peptide of the invention comprises one or more D-amino acids. In certain embodiments, a peptide of the invention comprises one or more non-natural amino acids (e.g., phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine).

In certain embodiments described herein, a peptide of the invention is modified to enable peptide purification and/or detection, as well as quantification of kinase activity in a particular assay.

For example, in certain embodiments, the peptide further comprises one or more lysine residues (e.g., 1, 2, 3, 4, 5, 6, 7, 8, 9, 10, or more). For example, an amino acid sequence of formula I may be modified to include one or more lysine residues within the peptide by either insertion or substitution. Alternatively, one or more lysine residues may be added to the N- or C-terminus of the peptide. Atoms within such lysine residues could be used to directly or indirectly link a peptide of the invention to an affinity capture agent (e.g., biotin) or a detectable agent, such as a fluorescent agent or a radioactive agent (e.g., a radionuclide loaded chelating agent).

In certain embodiments, a peptide of the invention comprises a second amino acid sequence linked to the N- or C-terminus of the first amino acid sequence through a peptide bond. In certain embodiments, the second amino acid sequence comprises one or more lysine residues (e.g., GGKGG (SEQ ID NO:21) or GGKKK (SEQ ID NO:22)). For example, in certain embodiments of the invention a peptide as described herein comprises/consists of an amino acid sequence having at least about 80%, 85%, 90%, 95%, 99% or 100% sequence identity to EDPIYVTLEGGKKK (SEQ ID NO:19) or DEAIYATVAGGKKK (SEQ ID NO:20).

In certain embodiments, the second amino acid sequence encodes a peptide tag (i.e., a fusion protein). In certain embodiments, the peptide tag is a fluorescent protein (e.g., Aquamarine, mCerulean, mTurquoise, mTurquoise2, CyPet, SCFP3A, Amber, mVenus, Ypet, SYFP2, SYFP2A, Clover, LSSmOrgange, mRuby2, ECFP, CFP, YFP, GFP, EGFP, Citrine, EYFP, mCherry and DsRed).

In certain embodiments, the second amino acid sequence encodes a lanthanide metal binding peptide. Fusion of such a tag to a peptide described herein would enable complexing with a lanthanide metal (e.g., La, Ce, Pr, Nd, Pm, Sm, Eu, Gd, Tb, Dy, Ho, Er, Tm, Yb, and Lu). Peptides that bind lanthanide metals are known in the art (e.g., Sueda et al., Analytical Biochemistry, 422(1):52-54; Martin et al., Methods Mol Biol 1248:201-220 (2015), which are incorporated by reference in their entireties). In certain embodiments, the lanthanide metal binding peptide is a terbium biding peptide (TBP).

In certain embodiments, a peptide as described herein is operably linked to an affinity capture agent. In certain embodiments, the affinity capture agent is biotin. In certain embodiments, the affinity capture agent is operably linked directly or indirectly through a lysine residue. For example, in certain embodiments, an affinity capture agent is operably linked to a second amino acid sequence comprising one or more lysine residues, wherein the second amino acid sequence is operably linked to the N- or C-terminus of a peptide described herein. For example, as described in Example 1, a -GGK$_{biotin}$GG tag (SEQ ID NO: 24) was linked to the C-terminus of a series of peptides described herein (see, Example 1). Thus, in certain embodiments, a peptide described herein further comprises a -GGK$_{biotin}$GG (SEQ ID NO: 24) tag operably linked to the N- or C-terminus of the peptide. In certain embodiments, a peptide as described herein comprises/consists of an amino acid sequence having at least about 80%, 85%, 90%, 95%, 99% or 100% sequence identity to EDPIYVTLEGGK$_{biotin}$GG (SEQ ID NO:11), DEAIYATVAGGK$_{biotin}$GG (SEQ ID NO:14) or EDDVYDSVPGGK$_{biotin}$GG (SEQ ID NO:16).

In certain embodiments, a peptide as described herein is operably linked to one or more detectable agents. In certain embodiments, when more than one detectable agent is linked to the peptide, the agents may be the same or different.

In certain embodiments, the detectable agent is a radioactive agent. For example, in certain embodiments, the detectable agent comprises a chelating agent. In certain embodiments, the chelating agent is loaded with a radionuclide.

In certain other embodiments, the detectable agent is a fluorescent group, which may also be called a "fluorescent tag" or a "fluorophore". A fluorophore is a molecule that absorbs light (i.e., excites) at a characteristic wavelength and emits light (i.e. fluoresces and emits a signal) at a second lower-energy wavelength. In certain embodiments, the fluorophore is one or more of the fluorophores listed in Table A.

TABLE A

| Probe | Excitation (nm) | Emission (nm) |
|---|---|---|
| Hydroxycoumarin | 325 | 386 |
| Alexa fluor | 325 | 442 |

TABLE A-continued

| Probe | Excitation (nm) | Emission (nm) |
|---|---|---|
| Aminocoumarin | 350 | 445 |
| Methoxycoumarin | 360 | 410 |
| Cascade Blue | (375); 401 | 423 |
| Pacific Blue | 403 | 455 |
| Pacific Orange | 403 | 551 |
| Lucifer yellow | 425 | 528 |
| Alexa fluor 430 | 430 | 545 |
| NBD | 466 | 539 |
| R-Phycoerythrin (PE) | 480; 565 | 578 |
| PE-Cy5 conjugates | 480; 565; 650 | 670 |
| PE-Cy7 conjugates | 480; 565; 743 | 767 |
| Red 613 | 480; 565 | 613 |
| PerCP | 490 | 675 |
| Cy2 | 490 | 510 |
| TruRed | 490, 675 | 695 |
| FluorX | 494 | 520 |
| Fluorescein | 495 | 519 |
| FAM | 495 | 515 |
| BODIPY-FL | 503 | 512 |
| TET | 526 | 540 |
| Alexa fluor 532 | 530 | 555 |
| HEX | 535 | 555 |
| TRITC | 547 | 572 |
| Cy3 | 550 | 570 |
| TMR | 555 | 575 |
| Alexa fluor 546 | 556 | 573 |
| Alexa fluor 555 | 556 | 573 |
| Tamara | 565 | 580 |
| X-Rhodamine | 570 | 576 |
| Lissamine Rhodamine B | 570 | 590 |
| ROX | 575 | 605 |
| Alexa fluor 568 | 578 | 603 |
| Cy3.5 581 | 581 | 596 |
| Texas Red | 589 | 615 |
| Alexa fluor 594 | 590 | 617 |
| Alexa fluor 633 | 621 | 639 |
| LC red 640 | 625 | 640 |
| Allophycocyanin (APC) | 650 | 660 |
| Alexa fluor 633 | 650 | 688 |
| APC-Cy7 conjugates | 650; 755 | 767 |
| Cy5 | 650 | 670 |
| Alexa fluor 660 | 663 | 690 |
| Cy5.5 | 675 | 694 |
| LC red 705 | 680 | 710 |
| Alexa fluor 680 | 679 | 702 |
| Cy7 | 743 | 770 |
| IRDye 800 CW | 774 | 789 |
| Alexa Fluor 488 | 490 | 525 |
| Alexa Fluor 647 | 650 | 665 |
| Brilliant Violet 421 | 405 | 421 |

Certain embodiments of the invention provide a peptide as described herein.

Certain embodiments, of the invention also provide a peptide generated using a method described herein.

Nucleic Acids, Expression Cassettes and Vectors

Certain embodiments of the invention also provide a nucleic acid sequence encoding a peptide as described herein.

Certain embodiments of the invention provide an expression cassette comprising a nucleic acid as described herein operably linked to a promoter.

Certain embodiments of the invention provide a vector comprising an expression cassette as described herein.

Certain embodiments of the invention provide a cell comprising a vector as described herein.

Compositions, Complexes and Kits

Certain embodiments of the invention provide a composition comprising one or more peptides as described herein and a kinase.

In certain embodiments, the composition further comprises radio-labeled ATP.

In certain embodiments, the composition further comprises a lanthanide metal. In certain embodiments, the lanthanide metal is selected from the group consisting of La, Ce, Pr, Nd, Pm, Sm, Eu, Gd, Tb, Dy, Ho, Er, Tm, Yb, and Lu. In certain embodiments, the lanthanide metal is Tb.

Certain embodiments of the invention provide a complex comprising one or more peptides as described herein and a lanthanide metal. In certain embodiments, the lanthanide metal is selected from the group consisting of La, Ce, Pr, Nd, Pm, Sm, Eu, Gd, Tb, Dy, Ho, Er, Tm, Yb, and Lu. In certain embodiments, the lanthanide metal is Tb.

Certain embodiments of the invention provide a kit comprising:

1) a peptide as described herein;
2) a lanthanide metal; and
3) instructions for measuring kinase activity using the peptide and the lanthanide metal. In certain embodiments, the kit further comprises one or more kinases.

Methods of Designing a Universal Substrate

Certain embodiments of the invention provide a method to design a peptide substrate which detects the activity of a plurality of protein tyrosine kinases (PTKs) (e.g., two or more PTK) comprising:

1) generating a candidate set of peptide substrates comprising the peptides of Formula I;
2) excluding one or more peptides from the candidate set, which are likely to not be phosphorylated by a plurality of kinases; and
3) screening the remaining peptides from step 2) for the ability to act as a substrate for a plurality of kinases (e.g., screening select peptides from the remaining peptides from step 2).

Certain embodiments of the invention provide a method to design a peptide substrate which detects the activity of a plurality of protein tyrosine kinases (PTKs) (e.g., two or more PTK) comprising:

1) analyzing the amino acid preference profiles for a panel of PTKs using the KINATEST_ID algorithm to generate a candidate set of peptide substrates;
2) excluding one or more peptides from the candidate set, which are likely to not be phosphorylated by a plurality of kinases; and
3) screening the remaining peptides from step 2) for the ability to act as a substrate for a plurality of kinases (e.g., screening select peptides from the remaining peptides from step 2).

In certain embodiments, the candidate set comprises peptides that have amino acids at each position that are preferred or neutral by all kinases within the panel. In certain embodiments, the candidate set comprises peptides that have amino acids at each position that are preferred by all kinases within the panel. Preferred, neutral and non-preferred amino acids may be designated based on a selected cut off value. For example, a certain amino acid residue may be considered "preferred" if it was found to be present in a peptide phosphorylated by a given kinase at a given position at, e.g., >2 standard deviations above the mean frequency of what would be expected given the sequence "background", determined from potential tyrosine-centered sequences in a given substrate peptide or protein and any known interacting partners or other unphosphorylated peptides present in a kinase reaction mixture but not phosphorylated by that kinase. Residues designated to be "neutral" to "slightly preferred" may be those exhibiting frequency values between, e.g., −1 to 2 standard deviations from the mean.

The KINATEST_ID algorithm is described in Lipchik, et al., *Journal of the American Chemical Society* 2015, 137, 2484, which is incorporated by reference in its entirety for all purposes. Briefly, the algorithm uses an input dataset of established literature-curated kinase substrate and non-substrate sequences to produce a position-specific scoring matrix (PSSM).

The PSSM provides a comprehensive assessment of the amino acid preferences for a given kinase at multiple positions flanking the tyrosine phosphosite. The Screener tool of the KINATEST-ID pipeline can calculate the sum of the PSSM-derived scores for each sequence relative to each kinase in the panel. It then ranks the sequences according to this score to predict potential "selectivity", in which a higher score means that more kinases are predicted to phosphorylate the sequence and a lower score meaning it may be more selective for a particular kinase. Accordingly, to generate a peptide substrate, which detects the activity of a plurality of protein tyrosine kinases (PTKs), peptide substrates with higher total summed scores are selected for further evaluation and sequences with relatively lower scores are excluded.

Thus, in certain embodiments, one or more peptides are excluded from the candidate set based on the sum of each position-specific scoring matrix (PSSM) for each kinase within the panel.

Assays for detecting kinase activity and the ability of a peptide to act as a kinase substrate are known in the art. In certain embodiments, the peptide substrates are screened using an assay described herein (e.g., an assay evaluating the ability of each kinase in the panel to phosphorylate the candidate peptide). In certain embodiments, the peptide substrates are screened using radioactive ATP, wherein substrates phosphorylated by a particular kinase are identified using the radioactive label.

In certain embodiments, the panel of PTKs comprises two or more kinases (e.g., 2, 3, 4, 5, 6, 7, 8, 9, 10, 15, 20, 25, 30, 35, 40, 45, 50, 55, 60, 65, 70, 75, 80, 85 or more PTKs). In certain embodiments, the panel comprises two or more receptor tyrosine kinases (RTKs). In certain embodiments, the panel comprises two or more non-receptor tyrosine kinases (NRTKs). In certain embodiments, the panel comprises at least one RTK and at least one NRTK.

In certain embodiments, the panel comprises two or more PTKs described herein.

In certain embodiments, the panel comprises two or more PTKs selected from the group consisting of AATK, ABL, ABL2, ACK, ALK, ARG, AXL, BLK, BMX, BTK, BRK, CSF1R, CSK, DDR1, DDR2, EGFR, EPHA1, EPHA2, EPHA3, EPHA4, EPHA5, EPHA6, EPHA7, EPHA8, EPHA10, EPHB1, EPHB2, EPHB3, EPHB4, EPHB6, ERBB2, ERBB3, ERBB4, FER, FES, FGFR1, FGFR2, FGFR3, FGFR4, FGR, FLT1, FLT3, FLT4, FMS, FRK, FYN, GSG2, HCK, IGF1R, ILK, INSR, INSRR, IR, IRAK4, ITK, JAK1, JAK2, JAK3, KDR, KIT (c-KIT), KSR1, LCK, LMTK2, LMTK3, LTK, LYN, MATK, c-MER, MERTK, MET (c-MET), MLTK, MST1R, MUSK, NPR1, NTRK1, NTRK2, NTRK3, PDGFRA, PDGFRB, PDK1/PDHK1, PDK2/PDHK2, PLK4, PTK2, PTK2B, PTK6, PTK7, PYK2, RET, ROR1, ROR2, ROS1, RYK, SGK493, SRC (c-Src), SRMS, STYK1, SYK, TEC, TEK, TEX14, TIE1, TNK1, TNK2, TNNI3K, TRKA, TRKB, TRPM7/CHAK1, TXK, TYK2, TYRO3, YES1 and ZAP70. In certain embodiments, the panel comprises two or more PTKs selected from the group consisting of ABL, ARG, BTK, CSK, FES, FYN, HCK, JAK2, LCK, LYN, PYK2, SRC, SYK and YES. In certain embodiments, the panel comprises ABL, ARG, BTK, CSK, FES, FYN, HCK, JAK2, LCK, LYN, PYK2, SRC, SYK and YES.

In certain embodiments, the candidate set comprises peptides of Formula I.

Certain embodiments of the invention also provide a method to design a peptide substrate which detects the activity of a plurality of kinases (e.g., two or more kinases) comprising:

1) computing a probability matrix by comparing frequencies of each amino acid at each amino acid position from −X to +Y, relative to the phosphorylated amino acid, from each of a plurality of known substrates for the kinase to the expected frequency for each of the amino acids at each amino acid position, wherein X and Y are independently selected from integers of from 3 to 6;

2) calculating a signal score for each amino acid in each position in a plurality of different peptides in a positional screening peptide library based on the ability of the kinases to phosphorylate the peptides;

3) forming a positional scoring matrix by multiplying the probability matrix of step 1) by the signal score of step 2);

4) using the results of step 3) to generate a candidate peptide library;

5) screening the ability of the plurality of kinases to phosphorylate peptides in the candidate peptide library; and 6) using the results from step 5) to select one or more peptides that are phosphorylated by a plurality of kinases.

Certain embodiments of the invention provide a method of designing a peptide substrate which detects the activity of a plurality of kinases (e.g., 2 or more) comprising using a method as described herein.

METHODS OF USE

As described herein peptides of the invention may be used in an assay to detect kinase activity in a system.

Thus, certain embodiments of the invention provide a method for detecting phosphorylation activity of a kinase, comprising contacting the kinase with peptide as described herein to provide a resulting mixture, wherein phosphorylation of the peptide indicates the kinase is active. In certain embodiments, phosphorylation is detected using an assay described herein.

Certain embodiments of the invention provide a method for detecting phosphorylation activity of a kinase, comprising:

1) contacting the kinase with a peptide as described herein to provide a resulting mixture;

2) measuring a signal from a detectable agent; and 3) detecting phosphorylation activity of the kinase when changes in the signal are detected as compared to a control.

Certain embodiments of the invention provide a method for detecting phosphorylation activity of a kinase, comprising:

1) contacting the kinase with a test peptide to provide a first resulting mixture;

2) measuring a signal from a detectable agent in the first resulting mixture;

3) contacting the kinase with a peptide as described in herein to provide a second resulting mixture;

4) measuring a signal from a detectable agent in the second resulting mixture; and 5) standardizing the signal from the first resulting mixture using the signal measurements from the second resulting mixture; and 6) detecting phosphorylation activity of the kinase when the standardized signal from the first resulting mixture is greater than a reference value.

Certain embodiments of the invention provide a method for identifying a substrate of a kinase, comprising:

1) contacting the kinase with a test peptide to provide a first resulting mixture;

2) measuring a signal from a detectable agent in the first resulting mixture;

3) contacting the kinase with a peptide as described herein to provide a second resulting mixture;

4) measuring a signal from a detectable agent in the second resulting mixture; and 5) standardizing the signal from the first resulting mixture using the signal measurements from the second resulting mixture; and 6) identifying the test peptide as a substrate of the kinase when the standardized signal from the first resulting mixture is greater than a reference value.

Certain embodiments of the invention provide a method to identity an inhibitor of a kinase comprising:

1) contacting a peptide as described herein, the kinase and a test compound to provide a resulting mixture;

2) measuring a signal from a detectable agent in the resulting mixture; and 3) identifying the test compound as an inhibitor of the kinase when changes in the signal are detected as compared to a control.

Certain embodiments of the invention provide a method to identity an inhibitor of a kinase comprising:

1) contacting a peptide as described herein and the kinase to provide a first resulting mixture;

2) measuring a signal from a detectable agent in the first resulting mixture;

3) contacting a peptide as described herein, the kinase and a test compound to provide a second resulting mixture;

4) measuring a signal from a detectable agent in the second resulting mixture; and 5) identifying the test compound as an inhibitor of the kinase when changes between the signal in the first resulting mixture and the signal from the second resulting mixture are detected (e.g., the signal from the second resulting mixture is less than the signal from the first resulting mixture).

In certain embodiments, the detectable agent(s) are operably linked to the peptide.

In certain embodiments, the method further comprises contacting the resulting mixture(s) with the detectable agent. For example, in certain embodiments the detectable agent is radioactive ATP.

In certain embodiments, a signal from the detectable agent(s) is associated with phosphorylation of the peptide by the kinase.

In certain embodiments, the detectable agent is a radioactive agent, a fluorescent agent or a lanthanide metal.

In certain embodiments, activity of the kinase is detected using a lanthanide metal. Thus, certain embodiments of the invention provide a method for detecting the activity of a kinase comprising:

1) contacting the kinase with a peptide as described herein to provide a resulting mixture;

2) contacting the resulting mixture with a lanthanide metal, under conditions such that a luminescent signal from the lanthanide metal is generated; and 3) detecting the luminescent signal, wherein the luminescent signal correlates with the activity of the kinase.

In certain embodiments, the method further comprises comparing the luminescent signal to a reference luminescent signal, wherein a change in the luminescent signal as compared to the reference luminescent signal is indicative of kinase activity.

In certain embodiments, the method further comprises detecting a reference luminescent signal from a lanthanide metal complexed with a control peptide, wherein the control peptide is non-phosphorylated.

In certain embodiments, the luminescent signal is detected by luminescence spectroscopy. In certain embodiments, the luminescent signal is detected by time-resolved luminescence spectroscopy. In certain embodiments, the peptide that complexes with a lanthanide metal gives a differentiable luminescent readout when it is phosphorylated.

Certain embodiments of the invention also provide a method to identify an inhibitor of a kinase comprising:

1) contacting a peptide as described herein, the kinase, and a test compound to provide a resulting mixture;

2) contacting the resulting mixture with a lanthanide metal; and 3) detecting a luminescent signal from the lanthanide metal, wherein the luminescent signal from the lanthanide metal correlates with the ability of the test compound to inhibit to the kinase.

In certain embodiments, the method further comprises comparing the luminescent signal to a reference luminescent signal, wherein a change in the luminescent signal as compared to the reference luminescent signal indicates the test compound is an inhibitor of the kinase.

In certain embodiments, the peptide described herein and the test compound competitively bind to the kinase.

In certain embodiments, the luminescent signal is detected by luminescence spectroscopy. In certain embodiments, the luminescent signal is detected by time-resolved luminescence spectroscopy. In certain embodiments, the peptide that complexes with a lanthanide metal gives a differentiable luminescent readout when it is phosphorylated.

In certain embodiments of a method described herein, the kinase is a kinase described herein. In certain embodiments of a method described herein, the kinase is selected from AATK, ABL, ABL2, ACK, ALK, ARG, AXL, BLK, BMX, BTK, BRK, CSF1R, CSK, DDR1, DDR2, EGFR, EPHA1, EPHA2, EPHA3, EPHA4, EPHA5, EPHA6, EPHA7, EPHA8, EPHA10, EPHB1, EPHB2, EPHB3, EPHB4, EPHB6, ERBB2, ERBB3, ERBB4, FER, FES, FGFR1, FGFR2, FGFR3, FGFR4, FGR, FLT1, FLT3, FLT4, FMS, FRK, FYN, GSG2, HCK, IGF1R, ILK, INSR, INSRR, IR, IRAK4, ITK, JAK1, JAK2, JAK3, KDR, KIT (c-KIT), KSR1, LCK, LMTK2, LMTK3, LTK, LYN, MATK, c-MER, MERTK, MET (c-MET), MLTK, MST1R, MUSK, NPR1, NTRK1, NTRK2, NTRK3, PDGFRA, PDGFRB, PDK1/PDHK1, PDK2/PDHK2, PLK4, PTK2, PTK2B, PTK6, PTK7, PYK2, RET, ROR1, ROR2, ROS1, RYK, SGK493, SRC (c-Src), SRMS, STYK1, SYK, TEC, TEK, TEX14, TIE1, TNK1, TNK2, TNNI3K, TRKA, TRKB, TRPM7/CHAK1, TXK, TYK2, TYRO3, YES1 and ZAP70.

In certain embodiments, the kinase is FGR and the peptide comprises a first amino acid sequence having at least 80% sequence identity to SEQ ID NO:7.

In certain embodiments, a peptide described herein may be used in a LRET assay, similar to those described in United States Patent Application Publication Number US2016/0097084, the content of which is hereby incorporated herein in its entirety.

In certain embodiments, the kinase is in a sample (e.g., a laboratory sample or a cell sample). In certain embodiments, the sample comprises one or more cells.

In certain embodiments of a method described herein, the kinase is in a cell.

In certain embodiments, the cell is a human cell. In certain embodiments, the human cell is derived from human bone marrow or human blood.

In certain embodiments, the cell is a cancer cell. In certain embodiments, the cancer is leukemia (e.g., chronic myeloid leukemia). In certain embodiments, the cell is a drug-resistant cancer cell.

Certain Definitions

The term "complex" refers to molecules or ensembles that consist of a central atom or ion, which is usually metallic, and a surrounding array of bound molecules, ions or moieties of a molecule. The surrounding array of bound molecules, ions or moieties of a molecule are usually electron donors attracted to the central atom or ion. The surrounding array of bound molecules, ions or moieties of a molecule are usually neutral or negatively charged.

The term "plurality" refers to 2 or more. For example, a plurality of kinases may refer to 2, 3, 4, 5, 6, 7, 8, 9, 10, 15, 20, 25, 30, 35, 40, 45, 50, 55, 60, 65, 70, 75, 80, 85 or more kinases.

The term "nucleic acid" refers to deoxyribonucleotides or ribonucleotides and polymers thereof in either single- or double-stranded form, composed of monomers (nucleotides) containing a sugar, phosphate and a base which is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) Nucl. Acids Res., 19:508; Ohtsuka et al. (1985) JBC, 260:2605; Rossolini et al. (1994) Mol. Cell. Probes, 8:91. A "nucleic acid fragment" is a fraction of a given nucleic acid molecule. Deoxyribonucleic acid (DNA) in the majority of organisms is the genetic material while ribonucleic acid (RNA) is involved in the transfer of information contained within DNA into proteins. The term "nucleotide sequence" refers to a polymer of DNA or RNA that can be single- or double-stranded, optionally containing synthetic, non-natural or altered nucleotide bases capable of incorporation into DNA or RNA polymers. The terms "nucleic acid," "nucleic acid molecule," "nucleic acid fragment," "nucleic acid sequence or segment," or "polynucleotide" may also be used interchangeably with gene, cDNA, DNA and RNA encoded by a gene.

By "portion" or "fragment," as it relates to a nucleic acid molecule, sequence or segment of the invention, when it is linked to other sequences for expression, is meant a sequence having at least 80 nucleotides, more preferably at least 150 nucleotides, and still more preferably at least 400 nucleotides. If not employed for expressing, a "portion" or "fragment" means at least 9, preferably 12, more preferably 15, even more preferably at least 20, consecutive nucleotides, e.g., probes and primers (oligonucleotides), corresponding to the nucleotide sequence of the nucleic acid molecules of the invention.

The term "amino acid," comprises the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also comprises natural and unnatural amino acids bearing a conventional amino protecting group (e.g. acetyl or benzyloxycarbonyl), as well as natural and unnatural amino acids protected at the carboxy terminus (e.g. as a ($C_1$-$C_6$) alkyl, phenyl or benzyl ester or amide; or as an α-methylbenzyl amide). Other suitable amino and carboxy protecting groups are known to those skilled in the art (See for example, T. W. Greene, *Protecting Groups In Organic Synthesis*; Wiley: New York, 1981, and references cited therein).

The terms "protein," "peptide" and "polypeptide" are used interchangeably herein. Polypeptide sequences specifically recited herein are written with the amino terminus on the left and the carboxy terminus on the right.

The invention encompasses isolated or substantially purified nucleic acid or protein compositions. In the context of the present invention, an "isolated" or "purified" DNA molecule or an "isolated" or "purified" polypeptide is a DNA molecule or polypeptide that exists apart from its native environment and is therefore not a product of nature. An isolated DNA molecule or polypeptide may exist in a purified form or may exist in a non-native environment such as, for example, a transgenic host cell. For example, an "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein or polypeptide having less than about 30%, 20%, 10%, 5%, (by dry weight) of contaminating protein. When the protein of the invention, or biologically active portion thereof, is recombinantly produced, preferably culture medium represents less than about 30%, 20%, 10%, or 5% (by dry weight) of chemical precursors or non-protein-of-interest chemicals. Fragments and variants of the disclosed nucleotide sequences and proteins or partial-length proteins encoded thereby are also encompassed by the present invention. By "fragment" or "portion" is meant a full length or less than full length of the nucleotide sequence encoding, or the amino acid sequence of, a polypeptide or protein.

"Naturally occurring" is used to describe an object that can be found in nature as distinct from being artificially produced. For example, a protein or nucleotide sequence present in an organism (including a virus), which can be isolated from a source in nature and which has not been intentionally modified by man in the laboratory, is naturally occurring.

"Wild-type" refers to the normal gene, or organism found in nature without any known mutation.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis that encode the native protein, as well as those that encode a polypeptide having amino acid substitutions. Generally, nucleotide sequence variants of the invention will have at least 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

"Conservatively modified variations" of a particular nucleic acid sequence refers to those nucleic acid sequences that encode identical or essentially identical amino acid sequences, or where the nucleic acid sequence does not encode an amino acid sequence, to essentially identical sequences. Because of the degeneracy of the genetic code, a large number of functionally identical nucleic acids encode any given polypeptide. For instance the codons CGT, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations" which are one species of "conservatively modified variations." Every nucleic acid sequence described herein which encodes a polypeptide also describes every possible silent variation, except where otherwise noted. One of skill will recognize that each codon in a nucleic acid (except ATG, which is ordinarily the only codon for methionine) can be modified to yield a functionally identical molecule by standard techniques. Accordingly, each "silent variation" of a nucleic acid which encodes a polypeptide is implicit in each described sequence.

"Recombinant DNA molecule" is a combination of DNA sequences that are joined together using recombinant DNA technology and procedures used to join together DNA sequences as described, for example, in Sambrook and Russell, Molecular Cloning: A Laboratory Manual, Cold Spring Harbor, N.Y.: Cold Spring Harbor Laboratory Press ($3^{rd}$ edition, 2001).

The terms "heterologous DNA sequence," "exogenous DNA segment" or "heterologous nucleic acid," each refer to a sequence that originates from a source foreign to the particular host cell or, if from the same source, is modified from its original form. Thus, a heterologous gene in a host cell includes a gene that is endogenous to the particular host cell but has been modified. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

A "homologous" DNA sequence is a DNA sequence that is naturally associated with a host cell into which it is introduced.

The term "gene" is used broadly to refer to any segment of nucleic acid associated with a biological function. Genes include coding sequences and/or the regulatory sequences required for their expression. For example, gene refers to a nucleic acid fragment that expresses mRNA, functional RNA, or a specific protein, including its regulatory sequences. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters. In addition, a "gene" or a "recombinant gene" refers to a nucleic acid molecule comprising an open reading frame and including at least one exon and (optionally) an intron sequence. The term "intron" refers to a DNA sequence present in a given gene which is not translated into protein and is generally found between exons.

A "vector" is defined to include, inter alia, any viral vector, plasmid, cosmid, phage or binary vector in double or single stranded linear or circular form which may or may not be self-transmissible or mobilizable, and which can transform prokaryotic or eukaryotic host either by integration into the cellular genome or exist extrachromosomally (e.g., autonomous replicating plasmid with an origin of replication).

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance or ampicillin resistance.

"Expression cassette" as used herein means a DNA sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. The expression of the nucleotide sequence in the expression cassette may be under the control of a constitutive promoter or of an inducible promoter that initiates transcription only when the host cell is exposed to some particular external stimulus. In the case of a multicellular organism, the promoter can also be specific to a particular tissue or organ or stage of development.

Such expression cassettes will comprise the transcriptional initiation region of the invention linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

The term "RNA transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

"Regulatory sequences" and "suitable regulatory sequences" each refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences that may be a combination of synthetic and natural sequences. As is noted above, the term "suitable regulatory sequences" is not limited to promoters. However, some suitable regulatory sequences useful in the present invention will include, but are not limited to constitutive promoters, tissue-specific promoters, development-specific promoters, inducible promoters and viral promoters.

"Promoter" refers to a nucleotide sequence, usually upstream (5') to its coding sequence, which controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions.

"Expression" refers to the transcription and/or translation in a cell of an endogenous gene, transgene, as well as the transcription and stable accumulation of sense (mRNA) or functional RNA. In the case of antisense constructs, expression may refer to the transcription of the antisense DNA only. Expression may also refer to the production of protein.

"Homology" refers to the percent identity between two polynucleotides or two polypeptide sequences. Two DNA or polypeptide sequences are "homologous" to each other when the sequences exhibit at least about 75% to 85% (including 75%, 76%, 77%, 78%, 79%, 80%, 81%, 82%, 83%, 84%, and 85%), at least about 90%, or at least about 95% to 99% (including 95%, 96%, 97%, 98%, 99%) contiguous sequence identity over a defined length of the sequences.

The following terms are used to describe the sequence relationships between two or more sequences (e.g., nucleic acids, polynucleotides or polypeptides): (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full length cDNA, gene sequence or peptide sequence, or the complete cDNA, gene sequence or peptide sequence.

(b) As used herein, "comparison window" makes reference to a contiguous and specified segment of a sequence, wherein the sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the sequence a gap penalty is typically introduced and is subtracted from the number of matches.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988) CABIOS, 4:11; the local homology algorithm of Smith et al. (1981) Adv. Appl. Math. 2:482; the homology alignment algorithm of Needleman and Wunsch, (1970) JMB, 48:443; the search-for-similarity-method of Pearson and Lipman, (1988) Proc. Natl. Acad. Sci. USA, 85:2444; the algorithm of Karlin and Altschul, (1990) Proc. Natl. Acad. Sci. USA, 87:2264, modified as in Karlin and Altschul, (1993) Proc. Natl. Acad. Sci. USA, 90:5873.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) Gene 73:237; Higgins et al. (1989) CABIOS 5:151; Corpet et al. (1988) Nucl. Acids Res. 16:10881; Huang et al. (1992) CABIOS 8:155; and Pearson et al. (1994) Meth. Mol. Biol. 24:307. The ALIGN program is based on the algorithm of Myers and Miller, supra. The BLAST programs of Altschul et al. (1990) JMB, 215:403; Nucl. Acids Res., 25:3389 (1990), are based on the algorithm of Karlin and Altschul supra.

Software for performing BLAST analyses is publicly available through the National Center for Biotechnology Information (available on the world wide web at ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized as described in Altschul et al. (1997) Nucleic Acids Res. 25:3389. Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g., BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See the world wide web at ncbi.nlm.nih.gov. Alignment may also be performed manually by visual inspection.

For purposes of the present invention, comparison of sequences for determination of percent sequence identity to another sequence may be made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of sequences means that a polynucleotide comprises a sequence that has at least 70%, 71%, 72%, 73%, 74%, 75%, 76%, 77%, 78%, or 79%, at least 80%, 81%, 82%, 83%, 84%, 85%, 86%, 87%, 88%, or 89%, at least 90%, 91%, 92%, 93%, or 94%, and at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, at least 80%, 90%, at least 95%.

(e)(ii) The term "substantial identity" in the context of a peptide indicates that a peptide comprises a sequence with at least 70%, 71%, 72%, 73%, 74%, 75%, 76%, 77%, 78%, or 79%, 80%, 81%, 82%, 83%, 84%, 85%, 86%, 87%, 88%, or 89%, at least 90%, 91%, 92%, 93%, or 94%, or 95%, 96%, 97%, 98% or 99%, sequence identity to the reference sequence over a specified comparison window. Optimal alignment is conducted using the homology alignment algorithm of Needleman and Wunsch, *J. Mol. Biol.* 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

By "variant" polypeptide is intended a polypeptide derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may results form, for example, genetic polymorphism or from human manipulation. Methods for such manipulations are generally known in the art.

Thus, the polypeptides of the invention may be altered in various ways including amino acid substitutions, deletions, truncations, and insertions. Methods for such manipulations are generally known in the art. For example, amino acid sequence variants of the polypeptides can be prepared by mutations in the DNA. Methods for mutagenesis and nucleotide sequence alterations are well known in the art. See, for example, Kunkel (1985) Proc. Natl. Acad. Sci. USA 82:488; Kunkel et al. (1987) Meth. Enzymol. 154:367; U.S. Pat. No. 4,873,192; Walker and Gaastra (1983) Techniques in Mol. Biol. (MacMillan Publishing Co., and the references cited therein. Guidance as to appropriate amino acid substitutions that do not affect biological activity of the protein of interest may be found in the model of Dayhoff et al., Atlas of Protein Sequence and Structure (Natl. Biomed. Res. Found. 1978). Conservative substitutions, such as exchanging one amino acid with another having similar properties, are preferred.

Thus, the genes and nucleotide sequences of the invention include both the naturally occurring sequences as well as mutant forms. Likewise, the polypeptides of the invention encompass naturally occurring proteins as well as variations and modified forms thereof. Such variants will continue to possess the desired activity. In certain embodiments, the deletions, insertions, and substitutions of the polypeptide sequence encompassed herein may not produce radical changes in the characteristics of the polypeptide. However, when it is difficult to predict the exact effect of the substitution, deletion, or insertion in advance of doing so, one skilled in the art will appreciate that the effect will be evaluated by routine screening assays.

Individual substitutions deletions or additions that alter, add or delete a single amino acid or a small percentage of amino acids (typically less than 5%, more typically less than 1%) in an encoded sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). In addition, individual substitutions, deletions or additions which alter, add or delete a single amino acid or a small percentage of amino acids in an encoded sequence are also "conservatively modified variations." "Operably-linked" refers to the association two chemical moieties so that the function of one is affected by the other, e.g., an arrangement of elements wherein the components so described are configured so as to perform their usual function. In certain embodiments, amino acid sequences are operably linked via a peptide bond.

In certain embodiments, a peptide of the invention is operably linked to an affinity capture agent or a detectable agent. The nature of the linkage is not critical provided the resulting conjugate retains the useful biological properties described herein (e.g., the peptide functions as a kinase substrate and the detectable or affinity capture agent retains its functionality).

In certain embodiments, the peptide is linked to the detectable agent or affinity capture agent through a direct bond.

In certain embodiments, the peptide is linked to the detectable agent or affinity capture agent through a linking group.

In one embodiment of the invention the linking group has a molecular weight of from about 20 daltons to about 20,000 daltons. In one embodiment of the invention the linking group has a molecular weight of from about 20 daltons to about 5,000 daltons. In one embodiment of the invention the linking group has a molecular weight of from about 20 daltons to about 1,000 daltons. In one embodiment of the invention the linking group has a molecular weight of from about 20 daltons to about 200 daltons.

In another embodiment of the invention the linking group has a length of about 5 angstroms to about 60 angstroms.

In another embodiment of the invention the linking group is a divalent, branched or unbranched, saturated or unsaturated, hydrocarbon chain, having from 1 to 25 carbon atoms, wherein one or more (e.g. 1, 2, 3, or 4) of the carbon atoms is optionally replaced by (—O—) or a divalent ring of formula:

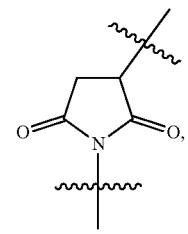 [SMILES: *C1CC(=O)N(*)C1=O]

and wherein the chain or ring is optionally substituted on carbon with one or more (e.g. 1, 2, 3, or 4) substituents selected from ($C_1$-$C_6$)alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, cyano, nitro, halo, hydroxy, oxo (=O), carboxy, aryl, aryloxy, heteroaryl, and heteroaryloxy.

In another embodiment of the invention a carboxylic acid of the detectable agent or affinity capture agent is reacted with an amine of the peptide to form an amide bond.

The invention will now be illustrated by the following non-limiting Example.

Example 1. In Silico Design and In Vitro Characterization of Universal Tyrosine Kinase Peptide Substrates The majority of the 90 human protein tyrosine kinases (PTKs) are understudied 'orphan' enzymes with few or no known substrates. Designing experiments aimed at assaying the catalytic activity of these PTKs has been a long-running problem. In the past, researchers have used polypeptides with a randomized 4:1 molar ratio of glutamic acid to tyrosine as general PTK substrates. However, these substrates are inefficient and perform poorly for many applications. In this work, the KINATEST-ID pipeline was applied for artificial kinase substrate discovery to design a set of candidate "universal" PTK peptide substrate sequences. Two unique peptide sequences from this set were identified, which had robust activity with a panel of 15 PTKs tested in an initial screen. Kinetic characterization with seven receptor and non-receptor PTKs confirmed these peptides to be efficient and general PTK substrates. The broad scope of these artificial substrates demonstrates that they should be useful as tools to probe understudied PTK activity.

Results

Several in silico methods have been reported that attempt to predict the substrate specificity of kinases (Kobe, et al., *Biochimica Et Biophysica Acta* 2005, 1754, 200; Miller, et al., *Science Signaling* 2008, 1, ra2; Mok, et al., *Science Signaling* 2010, 3, ra12; Saunders, et al., *BMC Bioinformatics* 2008, 9, 245). Previous work in our laboratory developed the KINATEST-ID platform for kinase artificial substrate discovery (Lipchik, et al., *Journal of the American Chemical Society* 2015, 137, 2484). This pipeline uses an input dataset of established literature-curated kinase substrate and non-substrate sequences to produce a position-specific scoring matrix (PSSM). The PSSM provides a comprehensive assessment of the amino acid preferences for a given kinase at multiple positions flanking the tyrosine phosphosite. An in silico library of candidate biosensor sequences can be generated and evaluated for predicted kinase specificity based on PSSMs derived from multiple kinases. In the work described herein, the KINATEST-ID workflow was used in a reversed fashion with the goal of designing a substrate that can be phosphorylated by as many PTKs as possible. A truly universal PTK substrate based on the actual substrate sequence preferences of a panel of PTKs would enable efficient activity assays to be designed, even for tyrosine kinases for which no substrates are currently known, and used in many applications from further study of orphan kinase biology to drug or tool compound discovery.

To identify a potential universal motif, the amino acid preference profiles for ABL, ARG BTK, CSK, FES, FYN, HCK, JAK2, LCK, LYN, PYK2, SRC, SYK and YES kinases were analyzed, and two approaches were taken to discover sequences with universal kinase coverage. The first in silico library of potential sequences was generated incorporating amino acid residues that were universally preferred. The second was generated using both commonly preferred and neutral amino acids. An initial set of nine peptides predicted to have broad specificity was synthesized and evaluated in kinase assays. The screen identified two hit sequences that were phosphorylated by the entire panel of PTKs tested. Further kinetic analysis confirmed these peptides to act generally as robust PTK substrates.

Figures 2, 3A:
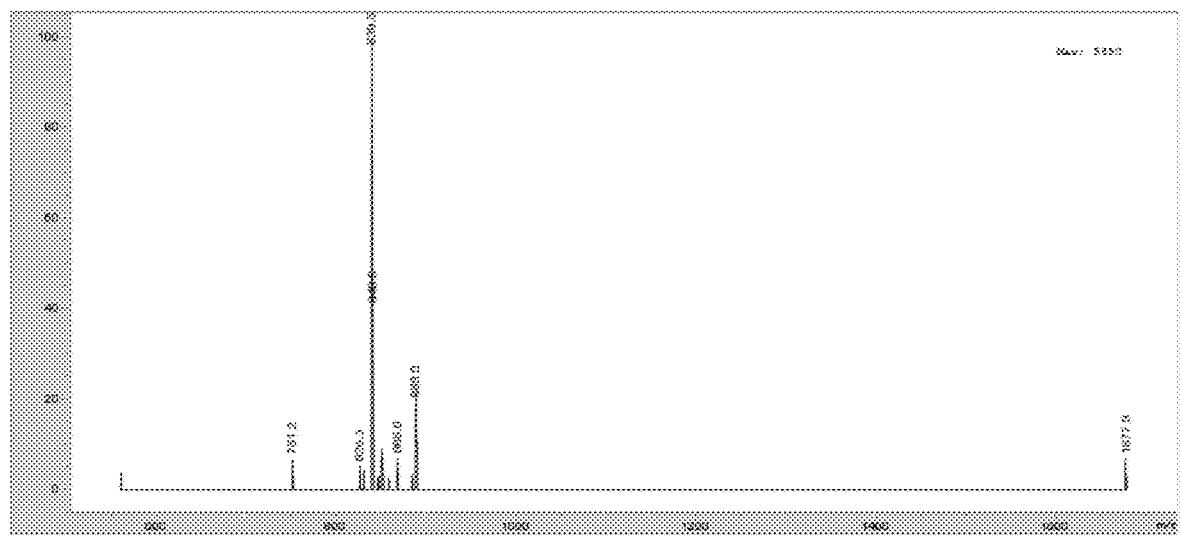

The amino acid preferences at positions neighboring the tyrosine phosphorylation site for each of the kinases in the panel were assembled and used as previously described (Lipchik, et al., *Journal of the American Chemical Society* 2015, 137, 2484). A certain amino acid residue was considered "favored" if it was found to be present at a given position at >2 standard deviations above the mean frequency of what would be expected given the "background" of potential tyrosine-centered sequences in a given substrate protein and any known interacting partners. Residues were designed to be "neutral" to "slightly favored" as those exhibiting frequency values between −1 to 2 standard deviations from the mean, and "disfavored" as those observed at frequencies <−1 standard deviations from the mean. In the case of HCK and PYK2, additional data from positional scanning peptide library screens were included as previously done (Bresler, et al., *Science Translational Medicine* 2011, 3, 108ra114). This data was used in two types of approaches, one "unbiased," (library 1) and one "biased" (library 2) by choosing certain options from the potential amino acids represented in the motif. In the "unbiased" approach, the amino acids that were first, second, and third most favored by the kinases, as well the single most commonly observed neutral amino acid, were selected to generate the first sequence library. In the "biased" approach, the second library was generated by manual selection of amino acids that were either favored or neutral, and that were most commonly represented in the motifs across all kinases in the panel. These parallel approaches were used to provide sequences that could balance the dual needs of substrate efficiency as well as universal tolerance. A summary of the preferred and neutral amino acids used to construct these libraries are shown in FIG. 2.

The sequences in the two libraries were obtained by generating every permutation of the particular amino acids at each position. The first library generated 663,552 potential sequences, while the second library generated 2,500 potential sequences. These sequences were then subjected to the Screener tool of the KINATEST-ID pipeline to score and rank their predicted likelihood as substrates for the set of PTKs in the panel, as previously described (Lipchik, et al., *Journal of the American Chemical Society* 2015, 137, 2484). This tool calculates the sum of the PSSM-derived scores for each sequence relative to each kinase in the panel. It then ranks the sequences according to this score to predict potential "selectivity", in which a higher score means that more kinases are predicted to phosphorylate the sequence and a lower score meaning it may be more selective for a particular kinase. The usual workflow for this process would be to filter the resulting list to remove sequences that do not have predicted specificity to a kinase of interest. However, the goal here was to identify sequences with the broadest possible activity, and so sequences were ranked according to highest total summed score for all screened kinases. With these curated libraries in hand, a set of sequences for synthesis and empirical testing was selected. The Screener tool removed the vast majority of the initial sequences from consideration, but still left several thousand high scoring sequences from which to choose. In the end, a total of nine different peptide sequences were chosen to form a pilot library for testing in a low-throughput kinase panel activity screen.

These peptides do not simply represent the nine highest scoring sequences that were output from Screener, but rather were selected based on a variety of factors, including considerations of additional details about known kinase preferences and particular chemical properties at certain positions (as discussed Lipchik, et al., *Journal of the American Chemical Society* 2015, 137, 2484; and Deng, et al., *Journal of Proteome Research* 2014, 13, 4339), to introduce a measure of diversity in this pilot library. The rationale for the sequence selection, synthetic procedures and characterization data for these peptides are included herein. The final list of peptides, their sequences and their summed score from Screener are included in Table 1.

TABLE 1

A list of the nine peptide sequences selected for synthesis and initial evaluation in a kinase panel activity screen. Each of these was synthesized with an C-terminal -GGK$_{biotin}$GG tag (SEQ ID NO: 24} for affinity capture purposes.

| Peptide | Sequence | Screener sum score |
|---|---|---|
| 1 | EDDEYVTPE (SEQ ID NO: 1) | 805.8 |
| 2 | EDPIYVTLE (SEQ ID NO: 2) | 933.4 |

TABLE 1-continued

A list of the nine peptide sequences selected for synthesis and initial evaluation in a kinase panel activity screen. Each of these was synthesized with an C-terminal -GGK$_{biotin}$GG tag (SEQ ID NO: 24) for affinity capture purposes.

| Peptide | Sequence | | | | Screener sum score |
|---|---|---|---|---|---|
| 3 | DEDIYGTPE | (SEQ | ID | NO: 3) | 1035.9 |
| 4 | DEPIYDTPE | (SEQ | ID | NO: 4) | 1067.2 |
| 5 | DEAIYATVA | (SEQ | ID | NO: 5) | 695.2 |
| 6 | DEPIYDTVE | (SEQ | ID | NO: 6) | 1055.5 |
| 7 | EDDVYDSVP | (SEQ | ID | NO: 7) | 987.1 |
| 8 | EDDEYISPE | (SEQ | ID | NO: 8) | 676.5 |
| 9 | EDDEYATPE | (SEQ | ID | NO: 9) | 667.1 |

This pilot library was then subjected to an initial screen to test their phosphorylation by a panel of 15 PTKs that included 12 non-receptor TKs (representing all 10 NRTK families) and 3 receptor TKs (representing 3 RTK families). Pilot peptides were assayed alongside several previously reported substrates that were designed to be specific to individual kinases. Conversion to product was monitored via incorporation of phosphate from [γ-$^{33}$P] radiolabeled adenosine triphosphate (ATP). These intensities were normalized to background and visualized as a heat map in FIG. 1. Peptides 2, 5 and 6 were phosphorylated by every PTK tested. By contrast, as previously reported, peptides that had been designed to specifically target individual kinases had more restricted reactivity. Peptides 2 and 5 had the highest average rate of phosphorylation across the entire panel of kinases (FIG. 1B), in most cases as high as or even higher than that observed for the positive control peptides for a given kinase, and were chosen for subsequent characterization.

To more fully characterize their properties as substrates for the PTKs tested, a follow-up kinetic analyses was performed with seven of the kinases from the panel (non-receptor TKs BTK, SYK, ABL and SRC, and receptor TKs ALK, EGFR and FLT3). Results for each kinase-peptide combination are summarized in Table 2. In most cases $K_m$ values were too high (>150 μM) for individual parameters to be accurately determined, and for the remaining kinase-substrate pairs the $K_m$ was in the double-digit μM range. As screening substrates are typically used at low μM concentrations, the $k_{cat}/K_m$ value (the rate constant at low sub-saturating peptide concentration, also called the specificity constant) was used to compare substrates, and from this value a lower limit for the $k_{cat}$ value was extrapolated where it could not be determined. While substantial variability was found between replicates for some kinases, relative rates of phosphorylation of the two peptides were highly consistent. For a given kinase, specificity constants for the two peptides were generally within two-fold of each other.

However, some kinases had a more substantial preference for either peptide 2 (EGFR) or peptide 5 (ABL and BTK). All non-receptor TKs had $k_{cat}/K_m$ values ≥960 M$^{-1}$ sec$^{-1}$ for at least one substrate. Kinetic parameters were generally less favorable than those reported for individually optimized consensus substrates (Deng, et al., *Journal of Proteome Research* 2014, 13, 4339), which was anticipated as generating peptides with broad reactivity necessitates the presence of sub-optimal residues at some positions. Somewhat surprisingly, it was found that for ABL and SRC, the catalytic parameters for peptides 2 and 5 rivaled those determined with consensus peptides. These results suggest that these two kinases are likely to be flexible in their primary sequence requirements. The lower activity for the three receptor TKs tested (FLT3, EGFR and ALK) in comparison with the NRTKs may reflect the basal activity of these kinases, each of which has low activity in the absence of cancer-associated activating mutations (Deng, et al., *Journal of Proteome Research* 2014, 13, 4339; Park, et al., *Biochemical Journal* 2012, 448, 417).

In conclusion, a modified workflow of the KINATEST-ID pipeline was used to design, completely in silico, a set of potential universal PTK substrate sequence motifs. It should be noted that none of the sequences in libraries 1 or 2 could be predicted to be comprehensively universal substrates based on the Screener filtering tool. The capabilities of Screener are limited by the input datasets for the PSSMs, which for understudied kinases could not be accurately modeled due to the small number (e.g. 15-20) of verified substrates identified in the literature. Nevertheless, the pilot collection of nine peptides yielded two hit sequences, a far better hit rate than typically achieved with randomized peptide libraries. These two hits, peptides 2 and 5, were first identified in an initial kinase activity screen and then further characterized with the determination of their kinetic parameters with a panel of seven PTKs representing a number of tyrosine kinase families. Both peptides were successful substrates for all kinases tested. Among the kinases that were examined, peptide 2 was generally preferred over peptide 5 for RTKs, while the reverse preference was seen for NRTKs, suggesting differential utility for distinct classes of PTK. It is anticipated that these universal PTK sequences will be valuable tools to assay enzymatic activity and screen for inhibitors in cases where suitable substrates have not been previously described. Furthermore, because these sequences have such broad activity, they could be used generally as quality control tools for recombinant tyrosine kinase preparations, and might enable more standardized benchmarking of sample quality and functional stability across kinases and preparations.

TABLE 2

Michaelis-Menten kinetic analysis for top two substrates. Mean ± sem of fits across experiment for all values; ND = not determined (rates linear over concentration range); $k_{cat}/K_M$ for data which could not be fitted was derived from the slope of the linear portion of the titration.

| | Peptide 2 | | | Peptide 5 | | | 2/5 |
|---|---|---|---|---|---|---|---|
| | $K_m$ (μM) | $k_{cat}$ (sec$^{-1}$) | $k_{cat}/K_m$ (sec$^{-1}$ M$^{-1}$) | $K_m$ (μM) | $k_{cat}$ (sec$^{-1}$) | $k_{cat}/K_m$ (sec$^{-1}$ M$^{-1}$) | $k_{cat}/K_m$ ratio |
| FLT3 | 41 ± 5 | 0.013 ± 0.004 | 304 ± 63 | 63.5 ± 0.2 | 0.014 ± 0.004 | 215 ± 54 | 1.43 ± 0.07 |
| ALK | >200 | >0.02 | 95 ± 19 | >200 | >0.02 | 79 ± 16 | 1.23 ± 0.02 |
| EGFR | >200 | >0.005 | 26 ± 5 | >200 | >0.001 | 5 ± 1 | 5.8 ± 0.2 |
| Abl | >200 | >4 | 20100 ± 2000 | 101 ± 19 | 16.5 ± 3.5 | 160400 ± 5700 | 0.13 ± 0.01 |

TABLE 2-continued

Michaelis-Menten kinetic analysis for top two substrates. Mean ± sem of fits across experiment for all values; ND = not determined (rates linear over concentration range); $k_{cat}/K_M$ for data which could not be fitted was derived from the slope of the linear portion of the titration.

| | Peptide 2 | | | Peptide 5 | | | 2/5 |
|---|---|---|---|---|---|---|---|
| | $K_m$ (μM) | $k_{cat}$ (sec$^{-1}$) | $k_{cat}/K_m$ (sec$^{-1}$ M$^{-1}$) | $K_m$ (μM) | $k_{cat}$ (sec$^{-1}$) | $k_{cat}/K_m$ (sec$^{-1}$ M$^{-1}$) | $k_{cat}/K_m$ ratio |
| BTK | 64 ± 11 | 0.061 ± 0.019 | 970 ± 240 | 84 ± 16 | 0.26 ± 0.08 | 3170 ± 840 | 0.31 ± 0.01 |
| Syk | >200 | >2 × 10−7 | 1080 ± 380 | >200 | >0.1 | 560 ± 120 | 1.8 ± 0.2 |
| Src | >200 | >40 | 17500 ± 3800 | >200 | >2 | 9500 ± 2800 | 0.52 ± 0.07 |

Materials and Methods

Rationale for Pilot Library Sequence Selection.

Peptide 1 represents the best scoring sequence in library 1 with a positive residue at the −1 position and a hydrophobic residue at the +1 position. Peptide 2 has a hydrophobic residue at both −1 and +1 (features common to many PTK motifs), and was also the highest scoring for JAK2 kinase in library 2, which was the kinase least likely to score well for most of the sequences evaluated. Peptide 3 was among the best scoring sequences in library 1 with a glycine at +1, and peptide 4 was the sequence with the highest overall score from library 1. Peptide 5 was not a sequence that was specifically generated in either library, but rather was modeled on similar high scoring sequences, combining features that were more general for most of the PTKs, and then modified to include an alanine at the +1 position. This was done because this position is known to be quite variable between PTKs, with some preferring specifically an aliphatic, an aromatic, or an acidic residue. The alanine was substituted to test whether it was able to be at least tolerated by all kinases. Peptide 6 was the highest scoring sequence in library 1 with a valine at the +3 position because most PTKs are known to favor a hydrophobic residue at that position. Peptide 7 was the highest scoring for JAK2 in library 1 with the valine at +3. Peptide 8 was the highest scoring sequence in library 2 with an acidic residue at −1 and an isoleucine residue at +1. And finally, peptide 9 was another sequence not generated by either library but was a slightly modified version of other high scoring sequences in which the +1 position was again an alanine residue.

Protein Expression and Purification.

The mammalian expression vector to produce the intracellular portion of human FLT3 fused to GST (GST-FLT3$^{564-993}$) was generated by PCR amplifying the encoding sequence and subcloning into the BamHI and NotI sites of pEBG-2T. Mammalian expression vectors to produce BTK, SRC and SYK as GST fusion proteins were previously described. GST-tagged kinases were expressed in HEK293T cells and purified by affinity chromatography using glutathione Sepharose 4B as described (Deng, et al., *Journal of Proteome Research* 2014, 13, 4339). His$_6$-EGFR$^{672-998}$ ("His$_6$" disclosed SEQ ID NO: 25) and His$_6$-ALK$^{1090-1416}$ ("His$_6$" disclosed SEQ ID NO: 25) were expressed and purified from Sf9 insect cells as described (Park, et al., *Biochemical Journal* 2012, 448, 417; Bresler, et al., *Science Translational Medicine* 2011, 3, 108ra114). Human ABL was purchased from Life Technologies.

Peptide Synthesis and Purification Methods.

The peptides were constructed on solid phase using standard Fmoc (9-fluorenylmethoxy-carbonyl) synthesis procedures. These were performed on a Symphony X peptide synthesizer (Protein Technologies) on a 50 μmol scale using commercially available Rink-amide-MBHA resin, protected amino acids (Peptide Solutions, LLC), 2-(6-chloro-1H-benzotria-zole-1-yl)-1,1,3,3-tetramethylaminium hexafluorophosphate (HCTU), N-methylmorpholine (NMM) (Protein Technologies), as well as dimethylformamide (DMF) (Iris Biotech GmbH) and dichloromethane (DCM) (Sigma Aldrich) solvents. The Fmoc groups were deprotected using a 20% v/v piperidine (Sigma Aldrich) solution in DMF for five minutes, then repeated again for another five minutes. The resin was then washed six times with 2 mL of DMF each time. The next amino acid in the sequence was added to the resin in 1.5 mL of a 200 mM solution followed by the addition of 1.5 mL of a solution containing 190 mM HCTU and 400 mM NMM. After 20 minutes, the resin was washed once with 2 mL of DMF, and then this coupling step was repeated, after which the resin was washed six times with DMF before the next iterative Fmoc deprotection. The biotinylated lysine couplings were performed only once with a reaction time of 2 hours total. After synthesis and removal of the last Fmoc group, the peptides were cleaved off the resin and the side-chains were globally deprotected for two hours using 5 mL of a solution of trifluoroacetic acid (TFA)/water/ethane dithiol/triisopropylsilane (TIS) 94:2.5:2.5:1 v/v (Sigma Aldrich). The peptides were precipitated in cold diethyl ether (Fisher Scientific) and the crude pellet was washed three times. The washed pellet was dissolved in acetonitrile/water 50:50 and lyophilized overnight to yield a powder. The crude peptides were analyzed by mass spectrometry (LC-MS) on an Agilent 1200 series LC and Agilent 6130 quadrupole ESI-MS. The peptides were then purified with a Hewlett-Packard 1100 preparative high performance liquid chromatography (HPLC) system on a Sepax Bio-C18 reverse-phase column (Sepax Technologies) with an increasing gradient of acetonitrile/0.1% TFA to water/0.1% TFA. The pure fractions were combined and lyophilized overnight.

Peptide Characterization Data.

The characterization data for the nine purified peptides (1-9) in the pilot library, as well as the purified peptides used for the kinetic characterization experiments (10-11), are included in FIGS. 3A-K. Peptides 1-9 were analyzed on an Agilent 6130 quadrupole ESI-MS by direct injection. Peptides 10-11 were analyzed on an Applied Biosystems-Sciex 5800 MALDI/TOF/TOF-MS.

Universal Kinase Substrate Screen.

Biotinylated peptides (10 μM final concentration) were arrayed in a 384-well plate in 18 μL reaction buffer (50 mM HEPES, pH 7.5, 150 mM NaCl, 10 mM MgCl$_2$, 1 mM DTT, 0.1% v/v Tween-20). Reactions were initiated by adding 2 L kinase (to 3-9 ng/μL) and [γ-$^{33}$P] ATP (to 50 μM, 0.025 μCi/μL) in reaction buffer. Plates were sealed and incubated at 30° C. for 30 min, and then 2 μL aliquots were transferred to streptavidin membrane (Promega SAM2 biotin capture membrane) using a pin-tool. Membranes were washed as described (Mok, et al., *Science Signaling* 2010, 3, ra12), dried and exposed to a phosphor screen. Incorporation of radiolabel was quantified by phosphor imaging using QuantityOne software (Bio-Rad). After background correction, data were normalized such that the peptide with the greatest signal was 100%. Normalized data from at least two separate experiments were averaged and converted to heatmaps using Excel (Microsoft).

Kinetic Analysis of Substrate Peptides.

For kinetic experiments, versions of the 2 and 5 peptides were synthesized in which Lys residues were substituted for the two C-terminal glycine residues. Reactions were set up as described above, with varying concentrations of peptides (1, 2.5, 5, 7.5, 15, 25, 50, 75, 100, and 150 μM). Final kinase concentrations were as follows: 0.3 ng/μL for ABL, BTK, SRC and SYK; 1.5 ng/μL for FLT3; 2.7 ng/μL for ALK and EGFR. At various incubation times (10, 20 and 30 min), 2 μL aliquots were transferred using a pin tool to P81 phosphocellulose paper (Reaction Biology), which was washed three times in 75 mM $H_3PO_4$, briefly washed in acetone and allowed to dry before exposing to a phosphor screen. Incorporation of radiolabel into peptides was quantified as above. After background correction, initial rates of reaction were determined by linear regression and fit to the Michaelis-Menten equation using Prism (GraphPad). For kinase-peptide pairs that had $K_m$ values too high to accurately fit the data to the Michaelis-Menten equation, $k_{cat}/K_m$ values were calculated from the slope of the linear portion of the Michaelis-Menten curve ([S]≤75 μM). Reported kinetic parameters are the average of three separate experiments except for FLT3 (two experiments).

Example 2. Kinase Screen of U2 and U5 Phosphorylation

Two universal tyrosine kinase substrate peptides (U2: EDPIYVTLEGGKKK (SEQ ID NO:19) and U5: DEAI-YATVAGGKKK (SEQ ID NO:20; kinase substrate portion in italics) were synthesized with two additional glycine residues (as a neutral linker) and three lysine residues (to assist with phosphocellulose membrane capture in the Reaction Biology "Hot Spot" radioactive ATP kinase assay). These were tested by Reaction Biology Corporation using their Hot Spot kinase assay service (Anastassiadis et al, *Nature Biotechnology*, v.29, pp. 1039-1045, 2011) in 50 kinase reactions (in technical duplicates for each) with different kinases. Kinase reactions were performed in reaction buffer containing 20 mM Hepes pH 7.5, 10 mM $MgCl_2$, 1 mM ethylene glycol-bis(β-aminoethyl ether)-N,N,N',N'-tetraacetic acid (EGTA), 0.02% Brij35, 0.02 mg/ml bovine serum albumin (BSA), 0.1 mM $Na_3VO_4$, 2 MM dithiothreitol (DTT), 1% dimethylsulfoxide (DMSO), enzyme, and either the U2 substrate or U5 substrate (20 μM). After combining all reaction buffer components with enzyme and/or substrate, ATP (plus a minimal proportion of $^{32}P$-labeled ATP) was added to initiate the reaction (50 μM). Samples were analyzed as described in Anastadiassis et al, 2011. Results from the U2 and U5 substrates were each compared to parallel reactions performed either without any substrate (Kinase Only).

Figure 4:
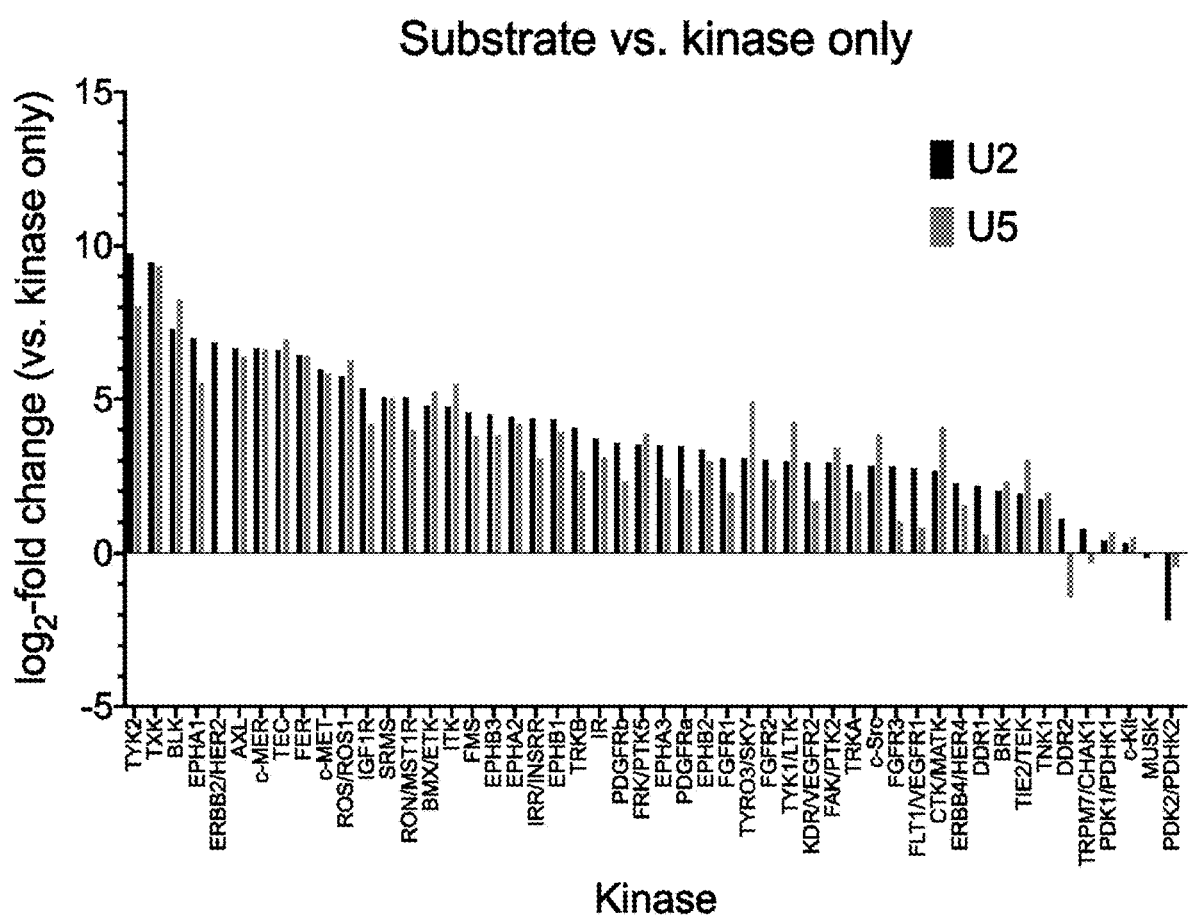
FIG. 4. Kinase screen of U2 (i.e., peptide 10; SEQ ID NO: 19) and U5 phosphorylation (i.e., peptide 11; SEQ ID NO:20). Log$_2$-fold change of activity (relative to the enzyme alone with no substrate) for each substrate with each kinase is shown.

Reaction Biology Corporation's standard assay substrate for each kinase was used as a positive control for enzyme activity (see, Anastassiadis et al, 2011). Results are shown in FIG. 4 as a $log_2$-fold change of activity (relative to the enzyme alone with no substrate) for each substrate with each kinase.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A peptide that is 9 to 50 amino acids in length and comprises a first amino acid sequence having at least 85% sequence identity to an amino acid sequence of formula Ia:

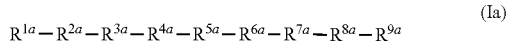
(Ia)

wherein:
$R^{1a}$ is selected from the group consisting of: E, D;
$R^{2a}$ is selected from the group consisting of: D, E;
$R^{3a}$ is P, A;
$R^{4a}$ is selected from the group consisting of: I;
$R^{5a}$ is Y;
$R^{6a}$ is selected from the group consisting of: V, A;
$R^{7a}$ is T;
$R^{8a}$ is selected from the group consisting of: L, V; and
$R^9$a is selected form the group consisting of: E, A;
or a salt thereof.

2. The peptide of claim 1, wherein first the amino acid sequence comprises an amino acid sequence of formula (Ia).

3. The peptide of claim 1, wherein the first amino acid sequence has at least 85% sequence identity to EDPIYVTLE (SEQ ID NO:2) or DEAIYATVA (SEQ ID NO:5).

4. The peptide of claim 1, wherein the first amino acid sequence is EDPIYVTLE (SEQ ID NO:2) or DEAIYATVA (SEQ ID NO:5).

5. A peptide comprising a first amino acid sequence having at least 85% sequence identity to EDDVYDSVP (SEQ ID NO:7).

6. The peptide of claim 1, further comprising a second amino acid sequence linked to the N- or C-terminus of the first amino acid sequence through a peptide bond.

7. The peptide of claim 6, wherein the second amino acid sequence comprises one or more lysine residues.

8. The peptide of claim 7, wherein the second amino acid sequence comprises GGKGG (SEQ ID NO:21) or GGKKK (SEQ ID NO:22).

9. The peptide of claim 8, which is EDPIYVTLEGGKKK (SEQ ID NO:19) or DEAIYATVAGGKKK (SEQ ID NO:20).

10. The peptide of claim 6, wherein the second amino acid sequence is a peptide tag sequence.

11. The peptide of claim 6, wherein the second amino acid sequence is a terbium binding peptide sequence.

12. The peptide of claim 1, which is 9 to 50 amino acids in length and consists of the first amino acid sequence having at least 85% sequence identity to the amino acid sequence of formula Ia.

13. The peptide of claim 1, operably linked to an affinity capture agent or a detectable agent.

14. The peptide of claim 1, which is a substrate for five or more of protein tyrosine kinases (PTKs).

15. The peptide of claim 1, which is a substrate for two or more PTKs selected from the group consisting of: AATK, ABL, ABL2, ACK, ALK, ARG, AXL, BLK, BMX, BRK, BTK, CSF1R, CSK, DDR1, DDR2, EGFR, EPHA1, EPHA2, EPHA3, EPHA4, EPHA5, EPHA6, EPHA7, EPHA8, EPHA10, EPHB1, EPHB2, EPHB3, EPHB4, EPHB6, ERBB2, ERBB3, ERBB4, FER, FES, FGFR1, FGFR2, FGFR3, FGFR4, FGR, FLT1, FLT3, FLT4, FMS, FRK, FYN, GSG2, HCK, IGF1R, ILK, INSR, INSRR, IR, IRAK4, ITK, JAK1, JAK2, JAK3, KDR, KIT, KSR1, LCK, LMTK2, LMTK3, LTK, LYN, MATK, c-MER, MERTK, MET, MLTK, MST1R, MUSK, NPR1, NTRK1, NTRK2, NTRK3, PDGFRA, PDGFRB, PDK1/PDHK1, PLK4, PTK2, PTK2B, PTK6, PTK7, PYK2, RET, ROR1, ROR2, ROS1, RYK, SGK493, SRC, SRMS, STYK1, SYK, TEC, TEK, TEX14, TIE1, TNK1, TNK2, TNNI3K, TRKA, TRKB, TRPM7/CHAK1, TXK, TYK2, TYRO3, YES1 and ZAP70.

16. The peptide of claim 1, which is a substrate for ABL, BTK, LYN, FGR, FYN, SRC, CSK, FES, ACK, EGFR, JAK3, ALK, FLT3, PYK2 and SYK.

17. A composition comprising a peptide as described in claim 1, a kinase and optionally, radio-labeled ATP.

18. A method for detecting phosphorylation activity of a kinase, comprising:
   1) contacting the kinase with a peptide as described in claim 1 to provide a resulting mixture;
   2) measuring a signal from a detectable agent; and
   3) detecting phosphorylation activity of the kinase when changes in the signal are detected as compared to a control.

19. A method for identifying a substrate of a kinase, comprising:
   1) contacting the kinase with a test peptide to provide a first resulting mixture;
   2) measuring a signal from a detectable agent in the first resulting mixture;
   3) contacting the kinase with a peptide as described in claim 1 to provide a second resulting mixture;
   4) measuring a signal from a detectable agent in the second resulting mixture; and
   5) standardizing the signal from the first resulting mixture using the signal measurements from the second resulting mixture; and
   6) identifying the test peptide as a substrate of the kinase when the standardized signal from the first resulting mixture is greater than a reference value.

20. A method to identity an inhibitor of a kinase comprising:
   1) contacting a peptide as described in claim 1, the kinase and a test compound to provide a resulting mixture;
   2) measuring a signal from a detectable agent in the resulting mixture; and
   3) identifying the test compound as an inhibitor of the kinase when changes in the signal are detected as compared to a control.

21. A method to design a peptide substrate which detects the activity of a plurality of protein tyrosine kinases (PTKs) comprising:
   1) generating a candidate set of peptide substrates comprising the peptides as described in claim 1;
   2) excluding one or more peptides from the candidate set, which are likely to not be phosphorylated by a plurality of kinases; and
   3) screening the remaining peptides from step 2) for the ability to act as a substrate for a plurality of kinases.

22. The peptide of claim 5, wherein the first amino acid sequence is EDDVYDSVP (SEQ ID NO:7).

23. The peptide of claim 5, which is EDDVYDSVP (SEQ ID NO:7).

24. The peptide of claim 1, which is EDPIYVTLE (SEQ ID NO:2).

25. The peptide of claim 1, which is DEAIYATVA (SEQ ID NO:5).

* * * * *

UNITED STATES PATENT AND TRADEMARK OFFICE
CERTIFICATE OF CORRECTION

PATENT NO. : 10,883,992 B2
APPLICATION NO. : 16/283412
DATED : January 5, 2021
INVENTOR(S) : Laurie L. Parker, Wei Cui and Benjamin Turk It is certified that error appears in the above-identified patent and that said Letters Patent is hereby corrected as shown below:

In the Claims

Column 44, Line 58, Claim 12, please delete "is 9 to 50 amino acids" and insert -- is 9 amino acids --;

Column 46, Line 9, Claim 20, please delete "identity" and insert -- identify -- therefor.

Signed and Sealed this
Eleventh Day of May, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 25

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Glu Asp Asp Glu Tyr Val Thr Pro Glu
1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Glu Asp Pro Ile Tyr Val Thr Leu Glu
1               5

```
<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asp Glu Asp Ile Tyr Gly Thr Pro Glu
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asp Glu Pro Ile Tyr Asp Thr Pro Glu
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Glu Ala Ile Tyr Ala Thr Val Ala
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asp Glu Pro Ile Tyr Asp Thr Val Glu
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Glu Asp Asp Val Tyr Asp Ser Val Pro
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 8

Glu Asp Asp Glu Tyr Ile Ser Pro Glu
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Glu Asp Asp Glu Tyr Ala Thr Pro Glu
1               5

<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Lys(biotin)

<400> SEQUENCE: 10

Glu Asp Asp Glu Tyr Val Thr Pro Glu Gly Gly Lys Gly Gly
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Lys(biotin)

<400> SEQUENCE: 11

Glu Asp Pro Ile Tyr Val Thr Leu Glu Gly Gly Lys Gly Gly
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Lys(biotin)

<400> SEQUENCE: 12

Asp Glu Asp Ile Tyr Gly Thr Pro Glu Gly Gly Lys Gly Gly
1               5                   10

<210> SEQ ID NO 13
<211> LENGTH: 14
<212> TYPE: PRT
<213> ORGANISM: Artificial Sequence
```

-continued

```
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Lys(biotin)

<400> SEQUENCE: 13

Asp Glu Pro Ile Tyr Asp Thr Pro Glu Gly Gly Lys Gly Gly
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Lys(biotin)

<400> SEQUENCE: 14

Asp Glu Ala Ile Tyr Ala Thr Val Ala Gly Gly Lys Gly Gly
1               5                   10

<210> SEQ ID NO 15
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Lys(biotin)

<400> SEQUENCE: 15

Asp Glu Pro Ile Tyr Asp Thr Val Glu Gly Gly Lys Gly Gly
1               5                   10

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Lys(biotin)

<400> SEQUENCE: 16

Glu Asp Asp Val Tyr Asp Ser Val Pro Gly Gly Lys Gly Gly
1               5                   10

<210> SEQ ID NO 17
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Lys(biotin)
```

```
<400> SEQUENCE: 17

Glu Asp Asp Glu Tyr Ile Ser Pro Glu Gly Gly Lys Gly Gly
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Lys(biotin)

<400> SEQUENCE: 18

Glu Asp Asp Glu Tyr Ala Thr Pro Glu Gly Gly Lys Gly Gly
1               5                   10

<210> SEQ ID NO 19
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Glu Asp Pro Ile Tyr Val Thr Leu Glu Gly Gly Lys Lys Lys
1               5                   10

<210> SEQ ID NO 20
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Asp Glu Ala Ile Tyr Ala Thr Val Ala Gly Gly Lys Lys Lys
1               5                   10

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Gly Lys Gly Gly
1               5

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Gly Lys Lys Lys
1               5
```

```
<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Glu Glu Glu Glu Tyr Glu Glu Glu Glu
1               5

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Lys(biotin)

<400> SEQUENCE: 24

Gly Gly Lys Gly Gly
1               5

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 25

His His His His His His
1               5
```